US012623003B2

(12) United States Patent
Shea et al.

(10) Patent No.: US 12,623,003 B2
(45) Date of Patent: May 12, 2026

(54) THREE-DIMENSIONAL MICROPOROUS SCAFFOLD DEVICE FOR CELL CULTURE

(71) Applicant: THE REGENTS OF THE UNIVERSITY OF MICHIGAN, Ann Arbor, MI (US)

(72) Inventors: Lonnie D. Shea, Ann Arbor, MI (US); Richard Youngblood, Ann Arbor, MI (US); Tadas Kasputis, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 1176 days.

(21) Appl. No.: 17/056,848

(22) PCT Filed: May 21, 2019

(86) PCT No.: PCT/US2019/033420

§ 371 (c)(1),
(2) Date: Nov. 19, 2020

(87) PCT Pub. No.: WO2019/226718

PCT Pub. Date: Nov. 28, 2019

(65) Prior Publication Data

US 2021/0228774 A1      Jul. 29, 2021

Related U.S. Application Data

(60) Provisional application No. 62/674,370, filed on May 21, 2018.

(51) Int. Cl.

| | |
|---|---|
| *A61L 27/38* | (2006.01) |
| *A61L 27/18* | (2006.01) |
| *A61L 27/36* | (2006.01) |
| *A61L 27/54* | (2006.01) |
| *A61L 27/56* | (2006.01) |
| *A61L 27/58* | (2006.01) |
| *C12N 5/071* | (2010.01) |

(52) U.S. Cl.
CPC ........... *A61L 27/3834* (2013.01); *A61L 27/18* (2013.01); *A61L 27/3633* (2013.01); *A61L 27/3895* (2013.01); *A61L 27/54* (2013.01); *A61L 27/56* (2013.01); *A61L 27/58* (2013.01); *C12N 5/0677* (2013.01); *C12N 5/0678* (2013.01); *C12N 2513/00* (2013.01); *C12N 2533/30* (2013.01); *C12N 2533/90* (2013.01)

(58) Field of Classification Search
CPC .. A61L 27/3834; A61L 27/18; A61L 27/3633; A61L 27/3895; A61L 27/54; A61L 27/56; A61L 27/58; C12N 5/0677; C12N 5/0678; C12N 2513/00; C12N 2533/30; C12N 2533/90
See application file for complete search history.

(56) References Cited

U.S. PATENT DOCUMENTS

| | | |
|---|---|---|
| 2014/0037749 A1 | 2/2014 | Shea et al. |
| 2014/0072510 A1 | 3/2014 | Shea et al. |
| 2016/0040132 A1 | 2/2016 | Sears et al. |
| 2018/0185550 A1 | 7/2018 | Kasputis et al. |

FOREIGN PATENT DOCUMENTS

| | | |
|---|---|---|
| WO | WO 2005/005607 | 1/2005 |
| WO | WO 2017/120486 | 7/2017 |

OTHER PUBLICATIONS

Yu, H., et al., "The rat pancreatic body tail as a source of a novel extracellular matrix scaffold for endocrine pancreas bioengineering," Journal of Biological Engineering 12:6. doi: 10.1186/s13036-018-0096-5. Apr. 27, 2018. (Year: 2018).*

Rezania, A., et al., "Reversal of diabetes with insulin-producing cells derived in vitro from human pluripotent stem cells," Nat Biotechnol 32(11): 1121-33. doi: 10.1038/nbt.3033. (Year: 2014).*

Wang, W., et al., "Development of Islet Organoids from H9 Human Embryonic Stem Cells in Biomimetic 3D Scaffolds," Stem Cells Dev 26(6): 394-404. doi: 10.1089/scd.2016.0115. Epub Jan. 17, 2017. (Year: 2017).*

Liu, J. M. H., et al., "Transforming growth factor-beta 1 delivery from microporous scaffolds decreases inflammation post-implant and enhances function of transplanted islets," Biomaterials 80: 11-19. doi: 10.1016/j.biomaterials.2015.11.065. Epub Dec. 2, 2015. (Year: 2015).*

Salvatori, M., et al., "Extracellular Matrix Scaffold Technology for Bioartificial Pancreas Engineering: State of the Art and Future Challenges," J Diabetes Sci Technol 8(1):159-169. doi: 10.1177/1932296813519558. (Year: 2014).*

Aguado et al., Extracellular matrix mediators of metastatic cell colonization characterized using scaffold mimics of the pre-metastatic niche. Acta Biomater. Mar. 2016;33:13-24.

(Continued)

*Primary Examiner* — Tracy Vivlemore
*Assistant Examiner* — Eric J Rogers
(74) *Attorney, Agent, or Firm* — Casimir Jones, S.C.; Rikki A. Hullinger

(57) ABSTRACT

An in vitro method of preparing insulin-producing cell clusters for transplantation into a subject, comprising (a) seeding pancreatic progenitor cells onto a three-dimensional, porous scaffold at a seeding density greater than about 12.5 million cells per $cm^3$ of scaffold and less than about 150 million cells per $cm^3$ of scaffold, wherein the scaffold comprises a plurality of pores having an average pore diameter greater than about 225 µm and less than about 550 pm, and (b) culturing the cells on the scaffold for more than about 3 days in culture medium to obtain insulin-producing cell clusters within the pores of the scaffold for transplantation into a subject. In exemplary aspects, the pancreatic progenitor cells are cells derived from pluripotent stem cells.

14 Claims, 7 Drawing Sheets

Specification includes a Sequence Listing.

(56)          References Cited

OTHER PUBLICATIONS

Aguado et al., Secretome identification of immune cell factors mediating metastatic cell homing. Sci Rep. Dec. 4, 2015;5:17566.

American Diabetes Association. Diagnosis and classification of diabetes mellitus. Diabetes Care. Jan. 2009;32 Suppl 1 (Suppl 1):S62-7.

Azarin et al., In vivo capture and label-free detection of early metastatic cells. Nat Commun. Sep. 8, 2015;6:8094.

Bittencourt et al., Insulin therapy in insulin resistance: could it be part of a lethal pathway? Atherosclerosis. Jun. 2015;240(2):400-1.

Blomeier et al., Polymer scaffolds as synthetic microenvironments for extrahepatic islet transplantation. Transplantation. Aug. 27, 2006;82(4):452-9.

Brennan et al., Long-Term Follow-Up of the Edmonton Protocol of Islet Transplantation in the United States. Am J Transplant. Feb. 2016;16(2):509-17.

Bruin et al., Maturation and function of human embryonic stem cell-derived pancreatic progenitors in macroencapsulation devices following transplant into mice. Diabetologia. Sep. 2013;56(9):1987-98.

Carvell et al., E-cadherin interactions regulate beta-cell proliferation in islet-like structures. Cell Physiol Biochem. 2007;20(5):617-26.

Chen et al., Human pluripotent stem cell culture: considerations for maintenance, expansion, and therapeutics. Cell Stem Cell. Jan. 2, 2014;14(1):13-26.

Cryer, PE. The barrier of hypoglycemia in diabetes. Diabetes. Dec. 2008;57(12):3169-76.

Daneman, Type 1 diabetes, Lancet. Mar. 11, 2006;367(9513):847-58.

Darribere et al., Integrins: regulators of embryogenesis. Biol Cell. Jan. 2000;92(1):5-25.

Dye et al., A bioengineered niche promotes in vivo engraftment and maturation of pluripotent stem cell derived human lung organoids. eLife 5 (Sep. 28, 2016): e19732. doi:10.7554/eLife.1973.

Farhat et al., Small human islets comprised of more β-cells with higher insulin content than large islets. Islets. Mar.-Apr. 2013;5(2):87-94.

Gibly et al., Extrahepatic islet transplantation with microporous polymer scaffolds in syngeneic mouse and allogeneic porcine models. Biomaterials. 2011;32:9677-84.

Gibly et al., Porous scaffolds support extrahepatic human islet transplantation, engraftment, and function in mice. Cell Transplant. 2013;22(5):811-9.

Hering et al., Phase 3 Trial of Transplantation of Human Islets in Type 1 Diabetes Complicated by Severe Hypoglycemia. Diabetes Care. Jul. 2016;39(7):1230-40.

Hlavaty et al., Enhancing human islet transplantation by localized release of trophic factors from PLG scaffolds. Am J Transplant. Jul. 2014;14(7):1523-32.

Jaques et al., Dual effect of cell-cell contact disruption on cytosolic calcium and insulin secretion. Endocrinology. May 2008;149(5):2494-505.

Jeong et al., Synthesis, characterization and protein adsorption behaviors of PLGA/PEG di-block co-polymer blend films. Colloids Surf B Biointerfaces. Oct. 1, 2000;18(3-4):371-379.

Jiang et al., Generation of insulin-producing islet-like clusters from human embryonic stem cells. Stem Cells. Aug. 2007;25(8):1940-53.

Kalra et al., Hypoglycemia: The neglected complication. Indian J Endocrinol Metab. Sep. 2013;17(5):819-34.

Kasputis et al., Microporous Polymer Scaffolds for the Transplantation of Embryonic Stem Cell Derived Pancreatic Progenitors to a Clinically Translatable Site for the Treatment of Type I Diabetes. ACS Biomater Sci Eng. May 14, 2018;4(5):1770-1778.

Kibbe. Handbook of Pharmaceutical Excipients, Third Edition, Pharmaceutical Press, London, UK, 2000. TOC only. 26 pages.

Kim et al., A novel culture technique for human embryonic stem cells using porous membranes. Stem Cells. Oct. 2007;25(10):2601-9.

Kroon et al., Pancreatic endoderm derived from human embryonic stem cells generates glucose-responsive insulin-secreting cells in vivo. Nat Biotechnol. Apr. 2008;26(4):443-52.

Kunisada et al., Small molecules induce efficient differentiation into insulin-producing cells from human induced pluripotent stem cells. Stem Cell Res. Mar. 2012;8(2):274-84.

Lablanche et al., Five-Year Metabolic, Functional, and Safety Results of Patients With Type 1 Diabetes Transplanted With Allogenic Islets Within the Swiss-French Gragil Network. Diabetes Care. Sep. 2015;38(9):1714-22.

Lehmann et al., Superiority of small islets in human islet transplantation. Diabetes. Mar. 2007;56(3):594-603.

Mendelsohn et al., Size-controlled insulin-secreting cell clusters. Acta Biomater. Dec. 2012;8(12):4278-84.

Michel et al., Influence of PEG architecture on protein adsorption and conformation. Langmuir. Dec. 20, 2005;21(26):12327-32.

Nair et al., Recapitulating endocrine cell clustering in culture promotes maturation of human stem-cell-derived β cells. Nat Cell Biol. Feb. 2019;21(2):263-274.

Nostro et al., Stage-specific signaling through TGFβ family members and WNT regulates patterning and pancreatic specification of human pluripotent stem cells. Development. Mar. 2011;138(5):861-71.

O'Connell et al., Multicenter Australian trial of islet transplantation: improving accessibility and outcomes. Am J Transplant. Jul. 2013;13(7):1850-8.

Pagliuca et al., Generation of functional human pancreatic β cells in vitro. Cell. Oct. 9, 2014;159(2):428-39.

Pagliuca et al., How to make a functional β-cell. Development. Jun. 2013;140(12):2472-83.

Pambianco et al., The 30-year natural history of type 1 diabetes complications: the Pittsburgh Epidemiology of Diabetes Complications Study experience. Diabetes. May 2006;55(5):1463-9.

Pepper et al., Posttransplant Characterization of Long-term Functional hESC-Derived Pancreatic Endoderm Grafts. Diabetes. May 2019;68(5):953-962.

Phillips et al., Directed differentiation of human embryonic stem cells into the pancreatic endocrine lineage. Stem Cells Dev. Aug. 2007;16(4):561-78.

Rao et al., Enhanced Survival with Implantable Scaffolds That Capture Metastatic Breast Cancer Cells in Vivo. Cancer Res. Sep. 15, 2016;76(18):5209-18.

Remington's Pharmaceutical Sciences, Sixteenth Edition, E. W. Martin. Mack Publishing Co., Easton, Pa., 1980. TOC only. 5 pages.

Rezania et al., Enrichment of human embryonic stem cell-derived NKX6.1-expressing pancreatic progenitor cells accelerates the maturation of insulin-secreting cells in vivo. Stem Cells. Nov. 2013;31(11):2432-42.

Rezania et al., Maturation of human embryonic stem cell-derived pancreatic progenitors into functional islets capable of treating pre-existing diabetes in mice. Diabetes. Aug. 2012;61(8):2016-29.

Rezania et al., Reversal of diabetes with insulin-producing cells derived in vitro from human pluripotent stem cells. Nat Biotechnol. Nov. 2014;32(11):1121-33.

Riopel et al., Collagen matrix support of pancreatic islet survival and function. Front Biosci (Landmark Ed). Jan. 1, 2014;19(1):77-90.

Rios et al., Evaluation of encapsulating and microporous nondegradable hydrogel scaffold designs on islet engraftment in rodent models of diabetes. Biotechnol Bioeng. Sep. 2018;115(9):2356-2364.

Rogers et al., E-cadherin and cell adhesion: a role in architecture and function in the pancreatic islet. Cell Physiol Biochem. 2007;20(6):987-94.

Ryan et al., Five-year follow-up after clinical islet transplantation. Diabetes. Jul. 2005;54(7):2060-9.

Salvay et al., Extracellular matrix protein-coated scaffolds promote the reversal of diabetes after extrahepatic islet transplantation. Transplantation. May 27, 2008;85(10):1456-64.

Sargent et al., Hydrodynamic modulation of embryonic stem cell differentiation by rotary orbital suspension culture. Biotechnol Bioeng. Feb. 15, 2010;105(3):611-26.

(56) References Cited

OTHER PUBLICATIONS

Sawhney et al., Bioerodible Hydrogels Based on Photopolymerized Poly(ethylene glycol)-co-poly (Hydroxy acid) Diacrylate Macromers. Macromolecules, 1993, 26, 581-587.

Serra et al., Process engineering of human pluripotent stem cells for clinical application. Trends Biotechnol. 30(6), Jun. 2012, 350-359.

Shapiro et al., International trial of the Edmonton protocol for islet transplantation. N. Engl. J. Med. 355 (2006) 1318-1330.

Shapiro et al., Islet transplantation in seven patients with type 1 diabetes mellitus using a glucocorticoid-free immunosuppressive regimen. N Engl J Med. Jul. 27, 2000;343(4):230-8.

Shim et al., Directed differentiation of human embryonic stem cells towards a pancreatic cell fate. Diabetologia. Jun. 2007;50(6):1228-38.

Tiwari et al., Therapeutic Targets for Diabetes Mellitus: An Update. Clin. Pharmacol. Biopharm. 3(1), 2014; 1-10.

Vegas et al., Long-term glycemic control using polymer-encapsulated human stem cell-derived beta cells in immune-competent mice. Nat Med. Mar. 2016;22(3):306-11.

Velazco-Cruz et al., Acquisition of Dynamic Function in Human Stem Cell-Derived β Cells. 12(2), Feb. 12, 2019, 351-365.

Wakae-Takada et al., Molecular basis for the regulation of islet beta cell mass in mice: the role of E-cadherin. Diabetologia. Apr. 2013;56(4):856-66.

Weizman et al., The effect of endothelial cells on hESC-derived pancreatic progenitors in a 3D environment. Biomater Sci. Nov. 30, 2014;2(11):1706-1714.

Yap et al., Collagen IV-modified scaffolds improve islet survival and function and reduce time to euglycemia. Tissue Eng Part A. Nov. 2013;19(21-22):2361-72.

Zhang et al., Highly efficient differentiation of human ES cells and iPS cells into mature pancreatic insulin-producing cells. Cell Res. Apr. 2009;19(4):429-38.

Zhao et al., Perfusion affects the tissue developmental patterns of human mesenchymal stem cells in 3D scaffolds. J Cell Physiol. May 2009;219(2):421-9.

Zhu et al., Monitoring C-Peptide Storage and Secretion in Islet β-Cells in Vitro and in Vivo. Diabetes. Mar. 2016;65(3):699-709.

International Search Report for PCT/US2019/033420, mailed Aug. 7, 2019, 11 pages.

* cited by examiner

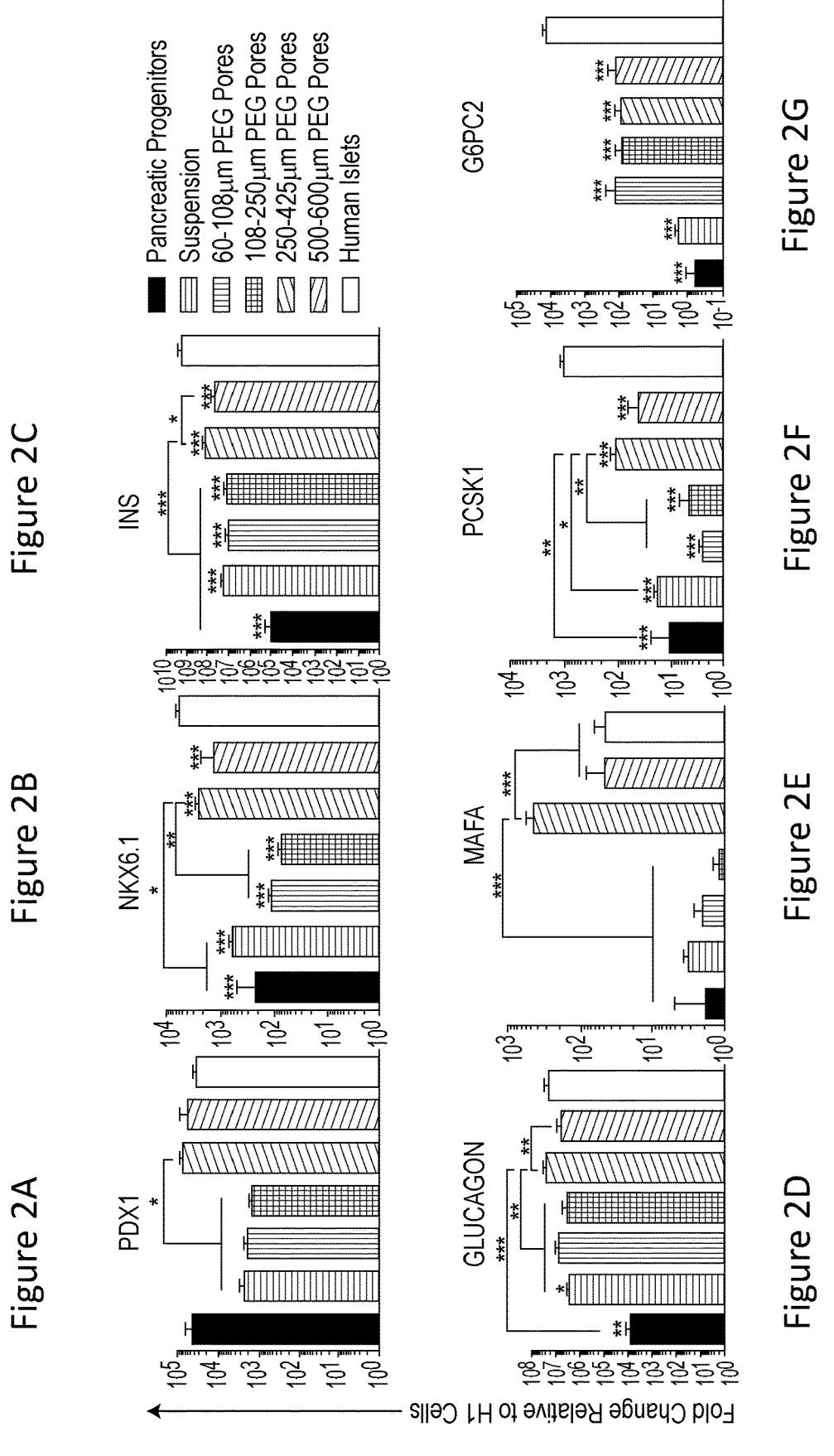

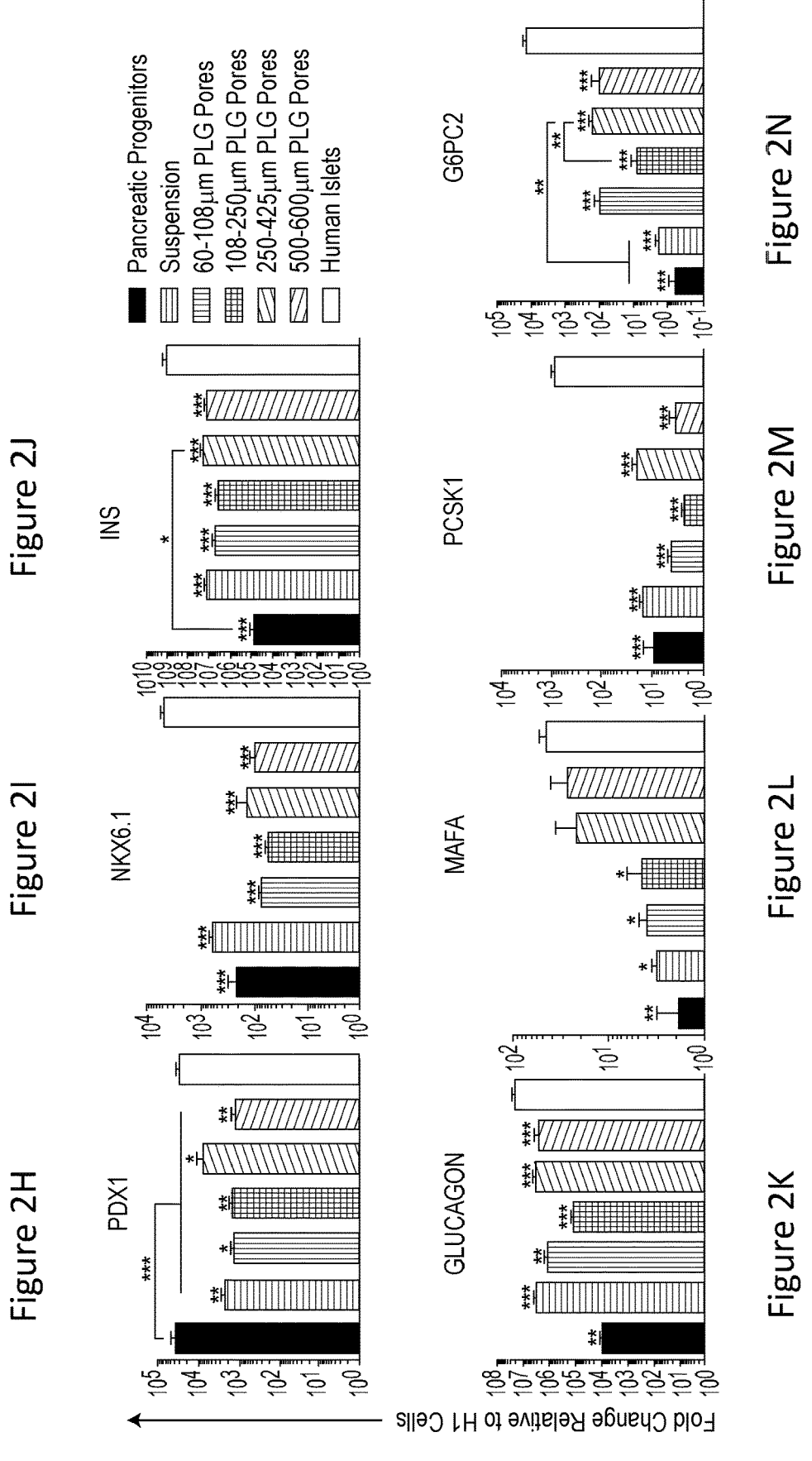

Figure 3C
Figure 3B
Figure 3A
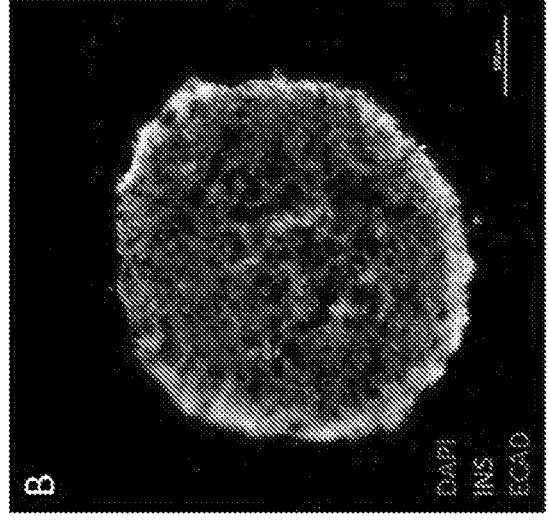
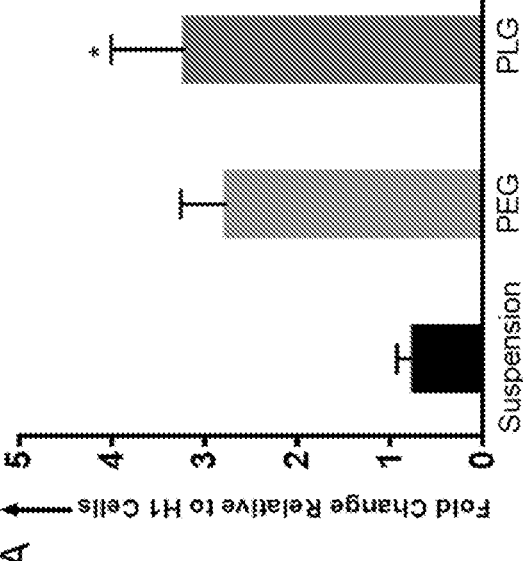

INS/Col IV/DAPI

INS/Lam/DAPI

INS/Fibr/DAPI

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 1
cctttcccat ggatgaagtc                                                    20

<210> SEQ ID NO 2
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 2
cgtccgcttg ttctcctc                                                      18

<210> SEQ ID NO 3
<211> LENGTH: 20
```

-continued

```
<212> TYPE: DNA
<213> ORGANISM: Artificial Sequence
<220> FEATURE:
<223> OTHER INFORMATION: Synthetic Polynucleotide

<400> SEQUENCE: 3
ggggatgaca gagagtcagg                                                    20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
cgagtcctgc ttcttcttgg                                                    20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
gagagcgaga agtgccaact                                                    20

<210> SEQ ID NO 6
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 6
ttctccttgt acaggtcccg                                                    20

<210> SEQ ID NO 7
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 7
ttctacacac ccaagacccg                                                    20

<210> SEQ ID NO 8
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 8
caatgccacg cttctgc                                                       17

<210> SEQ ID NO 9
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 9
```

-continued

```
tgctctctct tcacctgctc t                                       21

<210> SEQ ID NO 10
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 10
agctgccttg taccagcatt                                         20

<210> SEQ ID NO 11
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 11
ttgacgccga gagctacac                                          19

<210> SEQ ID NO 12
<211> LENGTH: 19
<212> TYPE: DNA
<213> ORGANISM: Artificial Sequence
<220> FEATURE:
<223> OTHER INFORMATION: Synthetic Polynucleotide

<400> SEQUENCE: 12
gaccggtgca atcttcaaa                                          19

<210> SEQ ID NO 13
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 13
ctctggctgc tggcatct                                           18

<210> SEQ ID NO 14
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 14
cgggtcatac tcagaggtcc                                         20

<210> SEQ ID NO 15
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 15
tggtatgtca tggtaaccgc                                         20

<210> SEQ ID NO 16
<211> LENGTH: 21
<212> TYPE: DNA
<213> ORGANISM: Artificial Sequence
```

-continued

```
<220> FEATURE:
<223> OTHER INFORMATION: Synthetic Polynucleotide

<400> SEQUENCE: 16
cactccaaag aaatgaccag g                                                    21
```

THREE-DIMENSIONAL MICROPOROUS SCAFFOLD DEVICE FOR CELL CULTURE

CROSS-REFERENCE TO RELATED APPLICATION

This application is a U.S. National Phase of International Application No. PCT/US2019/033420, filed May 21, 2019, which claims priority to U.S. Provisional Application No. 62/674,370, filed on May 21, 2018, the contents of which are incorporated herein by reference.

STATEMENT OF GOVERNMENT INTEREST

This invention was made with government support under CA186786, and CA231996 awarded by the National Institutes of Health. The government has certain rights in the invention.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: 4000 byte ASCII (Text) file named "53128A_Seqlisting.txt"; created on May 20, 2019.

FIELD OF THE INVENTION

The present disclosure relates generally to the fields of synthetic scaffold engineering and cell culturing. More specifically, the present disclosure relates to 3-dimensional (3D) synthetic scaffolds and uses thereof for the improved growth and differentiation of stem cells.

BACKGROUND

Type I diabetes (T1D) is a chronic metabolic disorder characterized by autoimmune destruction of the pancreatic β-cells that results in the need for life-long insulin therapy. This disease represents 5-10% of the diagnosed cases of diabetes, corresponding to more than 1.25 million individuals in the United States [Centers for Disease Control and Prevention 2017 Diabetes Report Card, CDC. (2015) 16]. Several secondary metabolic disorders can arise from this disease, as well, such as retinopathy, neuropathy, nephropathy, stroke and heart failure [Daneman, Type 1 diabetes, Lancet Lond. Engl. 367 (2006) 847-858. doi:10.1016/S0140-6736(06)68341-4; Tiwari et al., Clin. Pharmacol. Biopharm. 3 (2014). doi:10.4172/2167-065X.1000117]. Although exogenous insulin injections have decreased mortality, hypoglycemic events and macrovascular complications persist [Pambianco et al., Diabetes. 55 (2006) 1463-9; Bittencourt et al., Atherosclerosis. 240 (2015) 400-401. doi:10.1016/j.atherosclerosis.2015.04.013; and Kalra et al., Indian J. Endocrinol. Metab. 17 (2013) 819-834. doi: 10.4103/2230-8210.117219]. Thus, recent research has turned to cell-based therapies focused on replacing lost insulin-producing cells. Enthusiasm in cell replacement therapies for diabetes was driven, in part, by the progress in allogeneic islet transplantation with the Edmonton protocol [Ryan et al., Diabetes. 54 (2005) 2060-9; Shapiro et al., N. Engl. J. Med. 355 (2006) 1318-1330. doi:10.1056/NEJMoa061267; Hering et al., Diabetes Care. 39 (2016) 1230-1240. doi:10.2337/dc15-1988; Brennan et al., Long-Term Follow-Up of the Edmonton Protocol of Islet Transplantation in the United States, Am. J. Transplant. Off. J. Am. Soc. Transplant. Am. Soc. Transpl. Surg. 16 (2016) 509-517. doi:10.1111/ajt.13458, O'Connell et al., Australian Islet Transplant Consortium, Multicenter Australian trial of islet transplantation: improving accessibility and outcomes, Am. J. Transplant. Off. J. Am. Soc. Transplant. Am. Soc. Transpl. Surg. 13 (2013) 1850-1858. doi:10.1111/ajt.12250]. Recently, promising results from a European consortium of islet transplant centers showed excellent glycemic control and absence of hypoglycemia reported in approximately 80% of patients at 1 year and 60% at 5 years [Lablanche et al., Diabetes Care. 38 (2015) 1714-1722. doi:10.2337/dc15-0094]. However, the widespread application of islet transplantation has been tempered by the lack of availability of islets and the need for life-long immunosuppression [Stegall et al., Transplantation. 61 (1996) 1272-1274; Shapiro et al., Diabetes. 62 (2013) 1377-1378. doi:10.2337/db13-0019].

The lack of available islets has led to the investigation of human pluripotent stem cells (hPSCs) as an unlimited source of functional β-cells. Initial findings from the Kieffer and Baetge/D'Amour groups demonstrated the production of pancreatic progenitors and, subsequently, insulin-producing β-like cells in vitro. In the Kieffer lab, these cells could further differentiate following transplantation to normalize blood glucose levels after approximately 3-4 months [Rezania et al., Diabetes. 61 (2012) 2016-2029. doi:10.2337/db11-1711; Kroon et al., Nat. Biotechnol. 26 (2008) 443-452. doi:10.1038/nbt1393]. More recently, in vitro culture protocols have developed hPSC-derived β-cells that induce normoglycemia over shorter times after transplantation [Velazco et al., Stem Cell Rep. (2019). doi:10.1016/j.stemcr.2018.12.012; Rezania et al., Nat. Biotechnol. 32 (2014) 1121-1133. doi:10.1038/nbt.3033; Pagliuca et al., Cell. 159 (2014) 428-439. doi:10.1016/j.cell.2014.09.040; Pepper et al., Diabetes. (2018). doi:10.2337/db18-0788]. Additionally, suspension cultures utilized for aggregated hPSC-derived β-cell production provide procedures that are scalable to generate sufficient glucose-responsive cells [Velazco, 2019, supra, Pagliuca, 2014, supra].

While numerous protocols have been established, the in vitro production of β-cells can result in a heterogenous population consisting of polyhormonal endocrine cells in addition to monohormonal β-cells [Kroon, 2008, supra, Nostro et al., Dev. Camb. Engl. 138 (2011) 861-871. doi: 10.1242/dev.055236; Kunisada et al., Stem Cell Res. 8 (2012) 274-284. doi:10.1016/j.scr.2011.10.002]. Furthermore, the increasing culture volumes can influence the size of cell aggregates, which has previously been linked to apoptosis-related cell loss, cellular differentiation, and heterogeneity [Chen et al., Cell Stem Cell. 14 (2014) 13-26. doi:10.1016/j.stem.2013.12.005]. These challenges indicate the need to further investigate approaches that can promote maturation of insulin-producing β-cells.

hPSC-derived β-cells have currently been obtained through either a 2-dimensional (2D) monolayer culture that is subsequently transformed into large clusters on an air-liquid interface or as 3D aggregates in low attachment plates or suspension cultures. However, hPSC-derived β-cells grown in vitro in suspension cultures often lead to cell clusters that vary widely in size. hPSC-derived β-cells grown in vitro in 2D monolayer cultures suffer from the lack of a 3D microenvironment. In an in vivo setting, islets grow in clusters and are surrounded by a supportive extracellular matrix (ECM) which forms the 3D environment and offers a niche for cell adhesion, colonization, proliferation, and differentiation. Accordingly, there is a need for an improved in vitro cell culturing method, which provides the pancreatic niche environment and augments in vitro hPSC differentiation toward functional β-cells.

SUMMARY

Provided herein for the first time are data supporting that porous scaffolds may be used as a biomanufacturing platform to generate insulin-producing, glucose-responsive β-cells. Herein, it is shown that the microporous structure of scaffolds allows the 3D organization of cells into β-cell clusters, provides a high surface area-to-volume ratio for polymer-cell interactions, and allows nutrients to diffuse into the scaffold to support the growth of the seeded cells. The microporous scaffold may be employed to control the formation of clusters, and to favor cell-cell interactions that are influential in maturation. The hPSC-derived β-cells cultured on scaffolds were highly functional, demonstrating significantly increased gene expression levels of pancreatic endocrine hormones, insulin and glucagon, relative to pancreatic progenitor cells, and exhibiting higher insulin secretion and a higher percentage of insulin-positive cells, compared to hPSC-derived β-cells cultured in suspension cultures. Thus, hPSC-derived β-cells cultured on scaffolds demonstrated a higher efficiency at generating β-cells during differentiation. Also, as the hPSC-derived β-cells are ultimately purposed for transplantation into a subject, cells matured on scaffold maintain their niche that has been established within the pores, which support the cell structures during transplantation, whereas suspension clusters undergo manipulation during the transplantation process that may disrupt cell-cell and cell-matrix interactions.

Accordingly, the present disclosure is directed to the use of 3D synthetic scaffolds as substrates for the improved growth and differentiation of progenitor cells. In various aspects, these scaffolds are adapted for use in conjunction with existing cell culture lab plasticware. More specifically, the present disclosure is directed to microporous polymer scaffolds and their use as platforms for the efficient differentiation of hPSC (human pluripotent stem cells) to β-cells. Various aspects of the disclosure are directed to using microporous polymer scaffolds to promote the growth and differentiation of hPSC into glucose-responsive insulin-producing β-cells for the treatment of Type I diabetes. In various embodiments, this is accomplished through the sequential process of in vitro culture and then in vivo transplantation. Various embodiments are directed to the seeding of microporous scaffolds, either alone or in conjunction with various biologic matrix coatings, with hPSCs for the improved differentiation of said hPSCs into β-cells, immature β, or β-like cell types. The present disclosure also relates to the seeding of partially-differentiated β-cell progenitors onto scaffolds for further differentiation into more mature β-cell types.

The present disclosure provides an in vitro method of preparing insulin-producing cell clusters, comprising: (a) seeding pancreatic progenitor cells onto a three-dimensional, porous scaffold at a seeding density greater than about 12.5 million cells per cm³ of scaffold, wherein the scaffold comprises a plurality of pores having an average pore diameter greater than about 225 μm and less than about 600 μm; and (b) culturing the cells on the scaffold to obtain insulin-producing cell clusters. In exemplary aspects, the method comprises culturing the cells on the scaffold to obtain insulin-producing cell clusters within the pores of the scaffold. In various instances, step (a) of the presently disclosed method comprises seeding a volume of a solution comprising the pancreatic progenitor cells onto a three-dimensional, porous scaffold at, wherein the volume is not more than about 50 μL, optionally, not more than about 30 to about 35 μL. In various aspects, the pancreatic progenitor cells seeded onto the scaffold are Stage 4 pancreatic progenitor cells which were differentiated from Stage 0 human pluripotent stem cells. In exemplary aspects, the method comprises, prior to step (a), (i) treating the pancreatic progenitor cells with a cell dissociation agent, (ii) drying the scaffold, or (iii) a combination thereof. Optionally, step (b) comprises culturing the cells on the scaffold in vitro for at least or about 4 to about 10 days to obtain insulin-producing cell clusters, and optionally culturing the cells on the scaffold in vitro for more than or about 14 days. In various instances, step (b) comprises culturing the cells on the scaffold in vitro in an air-liquid interface cell culture system comprising a culture medium and a transwell membrane aligned with the air-liquid interface of the system, wherein the scaffold is positioned on top of the transwell membrane.

The present disclosure also provides a composition comprising a scaffold comprising insulin-producing cell clusters, wherein the insulin-producing cell clusters are prepared in accordance with any one of the presently disclosed in vitro methods of preparing insulin-producing cell clusters. The present disclosure also provides a use of the presently disclosed composition for treating a subject with an insulin deficiency. Further provided herein are methods of treating a subject with an insulin deficiency, comprising administering to the subject a presently disclosed composition.

A method of treating a patient with an insulin deficiency is additionally provided by the present disclosure. Optionally, the patient with an insulin deficiency suffers from diabetes. In exemplary embodiments, the method comprises: (a) seeding pancreatic progenitor cells onto a three-dimensional, porous scaffold at a seeding density greater than about 12.5 million cells per cm³ of scaffold, wherein the scaffold comprises a plurality of pores having an average pore diameter greater than about 225 μm and less than about 600 μm; (b) culturing the pancreatic progenitor cells on the scaffold to obtain insulin-producing cell clusters, optionally, wherein the insulin-producing cell clusters are in the pores of the scaffold; and (c) administering the scaffold comprising the insulin-producing cell clusters into the patient with the insulin deficiency.

BRIEF DESCRIPTION OF THE DRAWINGS

FIGS. 2A-2N demonstrate that augmenting scaffold pore sizes enhances pancreatic progenitor differentiation. Gene expression of pancreatic endocrine hormones, β-cell-associated transcriptional factors, and β-cell function-related proteins in hPSC-derived Stage 4 pancreatic progenitors and Stage 6 β-cells cultured on (FIGS. 2A-2G) PEG and (FIG. 2H-2N) PLG microporous scaffolds with varying pore sizes. (*$P \leq 0.05$, $P \leq 0.01$, *$P \leq 0.001$ for each condition versus human islets using one-way ANOVA with Dunnett test for multiple comparisons, n=6-7 biological replicates for all genes). Error bars represent the standard error of mean (SEM). FIGS. 2A and 2H graph the gene expression levels of PDX1. FIGS. 2B and 2I graph the gene expression levels of NKX6.1. FIGS. 2C and 2J graph the gene expression levels of Insulin. FIGS. 2D and 2K graph the gene expression levels of Glucagon. FIGS. 2E and 2L graph the gene expression levels of MAFA. FIGS. 2F and 2M graph the gene expression levels of PCSK1. FIGS. 2G and 2N graph the gene expression levels of G6PC2.

FIGS. 3A-3C demonstrate that scaffold culture influences E-cadherin interactions in β-cell clusters. The effect of scaffold cultures versus suspension control on ECAD in maturing β-cells was determined by quantitative RT-PCR. ECAD gene expression levels of cells cultured in suspension or on PEG and PLG microporous scaffolds (*$P \leq 0.05$ compared to suspension using one-way ANOVA with Dunnett test for multiple comparisons, n=4 biological replicates). Error bars represent the SEM. (FIG. 3AA) Immunofluorescent staining of suspension cluster (FIG. 3B) and PLG scaffold culture (FIG. 3C) for insulin (green), ECAD (red) and DAPI (blue).

(FIG. 4A) The stimulation index was calculated as the ratio of insulin release in high to low glucose concentrations (*$P \leq 0.05$, $P \leq 0.01$ compared to suspension, n=3-4 biological replicates) (FIG. 4B**). Error bars represent the SEM.

DETAILED DESCRIPTION

Figures 1A, 1B, 1C, 1D, 1E, 1F, 1G, 1H, 1I, 1J, 1K, 1L, 1M, 1N:
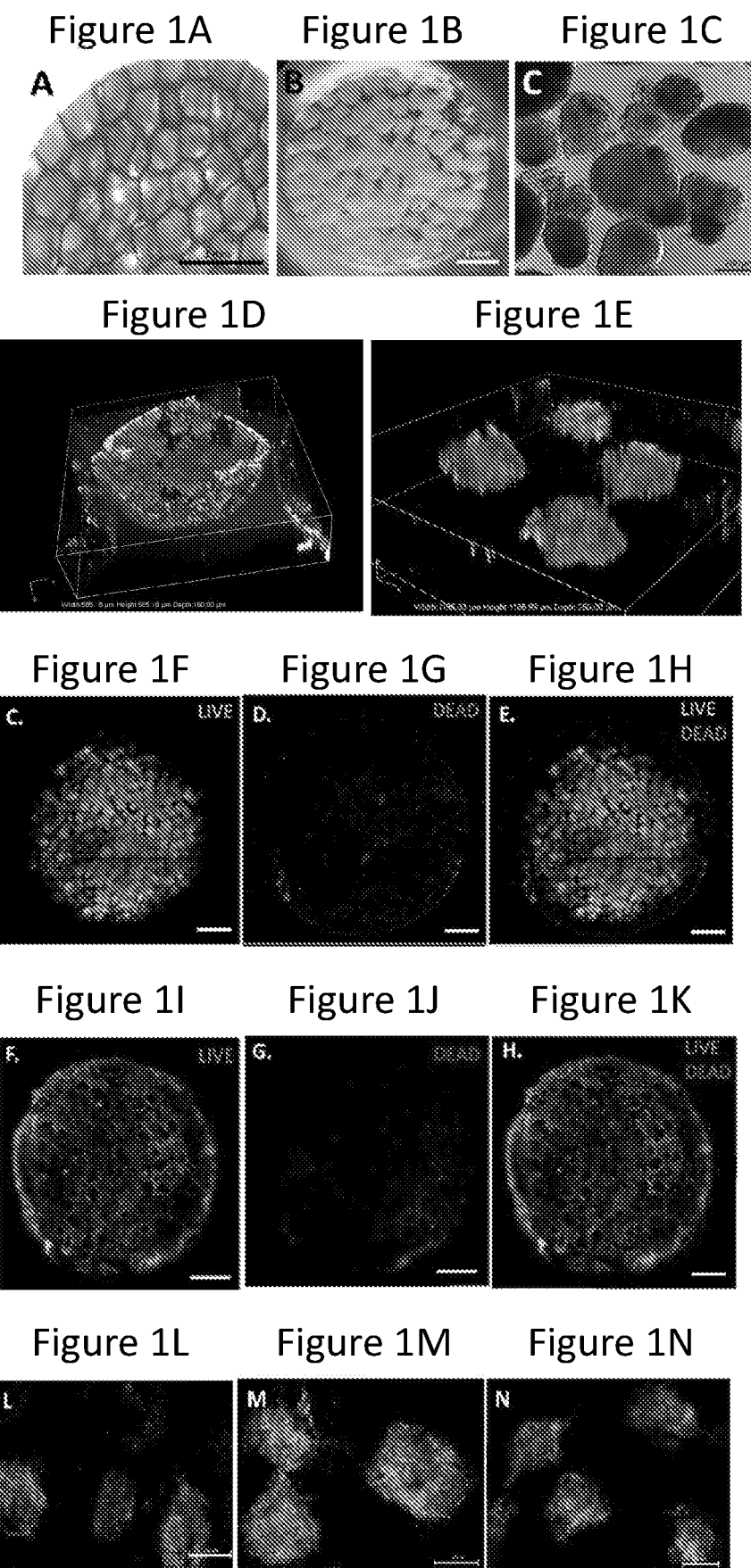
FIGS. 1A-1N demonstrate in vitro culturing of hPSC-derived pancreatic progenitors on microporous scaffolds. A scanning electron microscope (SEM) image of an empty porous PLG scaffold shows highly porous structure with 250-425 μm pores (FIG. 1A). Microscope images of PEG scaffold culture (FIG. 1B) and suspension culture (FIG. 1C) display formed β-cell clusters. Confocal imaging shows cell localization within a PEG scaffold pore at 12.5×10⁶ cells/cm³ (FIG. 1D) and multiple scaffold pores at 125×10⁶ cells/cm³ (FIG. 1E). Cells were stained 2 wks after seeding onto a PEG scaffold (FIGS. 1F-1H) and PLG scaffold (FIGS. 11-1K) and examined using a live/dead assay to demonstrate minimal cell death during culture. Confocal imaging shows cell clusters distributed within a 2 mm thick PEG scaffold pore at 0.5 mm depth (FIG. 1L), 1 mm depth (FIG. 1M) and 1.5 mm depth (FIG. 1N).

The present disclosure provides an in vitro method of preparing insulin-producing cell clusters, comprising: (a) seeding pancreatic progenitor cells onto a three-dimensional, porous scaffold at a seeding density greater than about 12.5 million cells per cm$^3$ of scaffold, wherein the scaffold comprises a plurality of pores having an average pore diameter greater than about 225 μm and less than about 600 μm; and (b) culturing the cells on the scaffold to obtain insulin-producing cell clusters within the pores of the scaffold for transplantation into a subject.

In exemplary instances, the seeding density is greater than about 15 million cells per cm$^3$ of scaffold or greater than about 20 million cells per cm$^3$ of scaffold. In various aspects, the seeding density is greater than 25 million cells per cm$^3$ scaffold, optionally, greater than 50 million cells per cm$^3$ scaffold. Optionally, the seeding density is greater than 75 million cells per cm$^3$ scaffold. In exemplary instances, the seeding density is greater than 100 million cells per cm$^3$ scaffold. In exemplary aspects, the seeding density is less than about 300 million cells per cm$^3$ of scaffold, optionally, less than about 250 million per cm$^3$ of scaffold. The seeding density is, in various aspects, about 15 million cells per cm$^3$ of scaffold to about 275 million cells per cm$^3$ of scaffold, about 20 million cells per cm$^3$ of scaffold to about 275 million cells per cm$^3$ of scaffold, about 25 million cells per cm$^3$ of scaffold to about 275 million cells per cm$^3$ of scaffold, about 50 million cells per cm$^3$ of scaffold to about 275 million cells per cm$^3$ of scaffold, about 75 million cells per cm$^3$ of scaffold to about 275 million cells per cm$^3$ of scaffold, about 100 million cells per cm$^3$ of scaffold to about 275 million cells per cm$^3$ of scaffold, about 125 million cells per cm$^3$ of scaffold to about 275 million cells per cm$^3$ of scaffold, about 150 million cells per cm$^3$ of scaffold to about 275 million cells per cm$^3$ of scaffold, about 175 million cells per cm$^3$ of scaffold to about 275 million cells per cm$^3$ of scaffold, about 200 million cells per cm$^3$ of scaffold to about 275 million cells per cm$^3$ of scaffold, about 225 million cells per cm$^3$ of scaffold to about 275 million cells per cm$^3$ of scaffold, about 250 million cells per cm$^3$ of scaffold to about 275 million cells per cm$^3$ of scaffold, about 15 million cells per cm$^3$ of scaffold to about 250 million cells per cm$^3$ of scaffold, about 15 million cells per cm$^3$ of scaffold to about 225 million cells per cm$^3$ of scaffold, about 15 million cells per cm$^3$ of scaffold to about 200 million cells per cm$^3$ of scaffold, about 15 million cells per cm$^3$ of scaffold to about 175 million cells per cm$^3$ of scaffold, about 15 million cells per cm$^3$ of scaffold to about 150 million cells per cm$^3$ of scaffold, about 15 million cells per cm$^3$ of scaffold to about 100 million cells per cm$^3$ of scaffold, about 15 million cells per cm$^3$ of scaffold to about 75 million cells per cm$^3$ of scaffold, about 15 million cells per cm$^3$ of scaffold to about 50 million cells per cm$^3$ of scaffold, or about 15 million cells per cm$^3$ of scaffold to about 25 million cells per cm$^3$ of scaffold. The seeding density is, in various aspects, about 100 million cells per cm$^3$ scaffold to about 250 million cells per cm$^3$ scaffold, optionally, about 100 million cells per cm$^3$ scaffold to about 200 million cells per cm$^3$ scaffold or about 100 million cells per cm$^3$ scaffold to about 150 million cells per cm$^3$ scaffold.

In exemplary aspects, the seeding step (step (a)) of the presently disclosed method comprises seeding a volume of a solution comprising the pancreatic progenitor cells onto a three-dimensional, porous scaffold at, wherein the volume is not more than about 100 μL (e.g., not more than about 75 μL or not more than about 50 μL). Optionally, the seeding step (step (a)) of the presently disclosed method comprises seeding a volume of a solution comprising the pancreatic progenitor cells onto a three-dimensional, porous scaffold at, wherein the volume is not more than about 35 μL or not more than about 30 μL. In some aspects, the volume of the solution comprising the pancreatic progenitor cells which is seeded on to the scaffold is about 5 μL to about 30 μL, about 5 μL to about 25 μL, about 5 μL to about 20 μL, about 5 μL to about 15 μL, about 5 μL to about 10 μL, about 10 μL to about 30 μL, about 15 μL to about 30 μL, about 20 μL to about 30 μL, or about 25 μL to about 30 μL.

In various instances, the pancreatic progenitor cells are seeded on both faces of the three-dimensional, porous scaffold.

In various instances, the pancreatic progenitor cells are Stage 4 pancreatic progenitor cells, e.g., Stage 4 pancreatic progenitor cells expressing PDX1 and NKX6.1. Optionally, the Stage 4 pancreatic progenitor cells are derived from pluripotent stem cells or embryonic stem cells. In some aspects, the pluripotent stem cells are human pluripotent stem cells (hPSCs), such as induced pluripotent stem cells (iPSCs) or human embryonic stem cells (hESCs). Optionally, the hPSCs are Stage 0 hPSCs, such as Stage 0 cells described in Rezania et al., Nat Biotechnol 32:1121-1133 (2014). In various instances, the Stage 4 pancreatic progenitor cells are cells differentiated from Stage 0 hPSCs. In various aspects, the Stage 4 pancreatic progenitor cells are cells obtained by exposing Stage 3 posterior foregut cells to MCDB 131 medium optionally supplemented with one or more of sodium bicarbonate, Glutamax, glucose, BSA, ascorbic acid, FGF7, SANT-1, retinoic acid, LDN193189, ITS-X, and TPB. In various aspects, the S3 cells are cultured in MCDB 131 medium supplemented with 2.5 g/l sodium bicarbonate, 1× Glutamax, 10 mM final glucose concentration, 2% BSA, 0.25 mM ascorbic acid, 2 ng/ml of FGF7, 0.25 mM SANT-1, 0.1 mM retinoic acid, 200 nM LDN193189, 1:200 ITS-X, and 100 nM TPB. The S3 cells were cultured in this medium for 3 days, as essentially described in Rezania et al., 2014, supra. In exemplary aspects, the S3 cells were obtained by culturing S2 cells, which in turn were obtained by culturing S1 cells, which in turn were obtained by culturing S0 cells, said culturing according to the protocols described in Rezania et al., 2014, supra, or Pagliuca et al., (2014), Cell. 2014 Oct. 9; 159 (2): 428-39. doi:10.1016/j.cell.2014.09.040.

In various aspects, the method of preparing the insulin-producing cells comprises, before step (a), culturing Stage 3 posterior foregut cells in a differentiation medium to obtain Stage 4 pancreatic progenitor cells expressing PDX1 and NKX6.1. In various instances, the method of preparing the insulin-producing cells comprises, before step (a), obtaining Stage 3 posterior foregut cells by culturing Stage 2 primitive gut tube cells in differentiation medium and then culturing Stage 3 posterior foregut cells in a differentiation medium to obtain Stage 4 pancreatic progenitor cells expressing PDX1 and NKX6.1. In exemplary instances, the method of preparing the insulin-producing cells comprises, before step (a), obtaining Stage 2 primitive gut tube cells by culturing Stage 1 definitive endoderm cells in a differentiation medium, then culturing Stage 2 primitive gut tube cells in differentiation medium to obtain Stage 3 cells, and then culturing Stage 3 posterior foregut cells in a differentiation medium to obtain Stage 4 pancreatic progenitor cells expressing PDX1 and NKX6.1. In exemplary aspects, the method further comprises before step (a), obtaining Stage 1 definitive endoderm cells by culturing Stage 0 hESC cells in a differentiation medium, then culturing the Stage 1 definitive endoderm cells in a differentiation medium to obtain Stage 2 primitive gut tube cells, then culturing Stage 2 primitive gut tube cells in differentiation medium to obtain Stage 3 cells, and then culturing Stage 3 posterior foregut cells in a differentiation medium to obtain Stage 4 pancreatic progenitor cells expressing PDX1 and NKX6.1. Such steps are known in the art and are described herein in the EXAMPLES. Optionally, Stage 0 hPSCs are cultured in differentiation medium for about 8 to about 12 days, optionally, about 10 days, to obtain Stage 4 pancreatic precursor cells. Optionally, the method further comprises (i) culturing Stage 0 hPSCs to obtain Stage 1 cells, (ii) culturing Stage 1 cells to obtain Stage 2 cells, (iii) culturing Stage 2 cells to obtain Stage 3 cells, (iv) culturing Stage 3 cells to obtain Stage 4 pancreatic progenitor cells, or (v) a combination thereof, wherein, when the method comprises all of (i) to (iv), the method comprises culturing for about 8 to about 12 days, optionally, about 10 days.

Also, in various aspects, prior to step (a), the method comprises (i) treating the pancreatic progenitor cells with a cell dissociation agent, (ii) drying the scaffold, or (iii) a combination thereof. Treating the pancreatic progenitor cells with the cell dissociation agent disperses the cells into single cells (vs. an aggregated form of cells). In various aspects, the dissociation agent is gentle cell dissociation reagent (STEM-CELL technologies, Cat. #07174), TrypLE Express (ThermoFisher Scientific, Waltham, MA), Accutase™ (BioLegend®, San Diego, CA), or trypsin. In various instances, the dissociation agent is trypsin or TrypLE Express. Such a step in known in the art and are described herein in Example 3. In exemplary aspects, prior to step (a), the scaffold is prepared for cell seeding, and, in various aspects, the scaffold is washed in cell media solution then briefly dried on sterile gauze. In various aspects, the scaffold is placed on the gauze for about less than or about 1 minute, optionally, for about 15 seconds to about 30 seconds. In various instances, the scaffold is not coated with one or more ECM proteins prior to the seeding step. In exemplary aspects, the scaffold, immediately prior to the seeding step, is substantially free of any proteins, e.g., ECM proteins. Thus, step (a) in various aspects comprises seeding the pancreatic progenitor cells onto an ECM protein-free, three-dimensional, porous scaffold, optionally, wherein the scaffold is not coated with one or more ECM proteins prior to the seeding step or optionally wherein the scaffold is protein-free. In some aspects, the only source of ECM proteins present in the culture comprising the cells seeded onto the scaffold are ECM proteins expressed and secreted by the seeded cells.

On-Scaffold Cell Cultures

In various aspects, step (b) comprises culturing the cells on the scaffold in vitro for at least or about 3 days, e.g., about 4 to about 10 days or more. In exemplary instances, step (b) comprises culturing the cells on the scaffold in vitro for more than 10 days, e.g., more than about 11 days, more than about 12 days, more than about 13 days, more than or about 14 days, to obtain insulin-producing cell clusters, and optionally culturing the cells on the scaffold in vitro for longer, e.g., about 15 days to about 20 days (e.g., about 15 days, about 16 days, about 17 days, about 18 days, about 19 days, about 20 days), or possibly even longer, e.g., about 21 days, about 22 days, about 23 days, about 24 days.

In exemplary instances, step (b) comprises culturing the cells on the scaffold in vitro in an air-liquid interface cell culture system comprising a culture medium and a Transwell membrane (or like insert) aligned with the air-liquid interface of the system, wherein the scaffold is positioned on top of the membrane. Without being bound to any particular theory, this configuration of the scaffold positioned atop the membrane which is aligned with the air-liquid interface of the system provides a better environment for achieving cell maturation and formation of cell clusters in the scaffolds, compared to a scaffold submerged in culture medium in a container. Suitable air-liquid interface cell culture systems and membranes for use in such systems are known in the art and include, e.g., Corning® HTS Transwell®-24 well permeable supports. See, e.g., Kim et al., Stem Cells 2601-2609 (2007). In various aspects, step (b) comprises placing the scaffolds comprising the seeded cells on a transwell membrane or a transwell insert in well of a multi-well plate. In some aspects, the plane of the membrane is positioned to align with the air-liquid interface of the cell culture system. In exemplary aspects, the system comprises Stage 5 (S5) media and step (b) comprises culturing the S4 cells on the transwell membrane at the air-liquid interface wherein the liquid is S5 medium. Optionally, the cells are cultured on the scaffold in this system for 3 days to obtain S5 pancreatic endocrine precursor cells that are PDX1$^+$/NKX6.1$^+$/NEUROD1$^+$. Optionally, the S5 medium comprises MCDB medium supplemented with 1.5 g/l sodium bicarbonate, 1× Glutamax, 20 mM final glucose concentration, 2% BSA, 0.25 mM SANT-1, 0.05 mM retinoic acid, 100 nM LDN193189, 1:200 ITS-X, 1 mM T3 (3,3',5-Triiodo-I-thyronine sodium salt, Sigma, T6397), 10 mM ALK5 inhibitor II (Enzo Life Sciences, NY, Cat #ALX-270-445), 10 mM zinc sulfate (Sigma, Z0251) and 10 mg/ml of heparin (Sigma, H3149).

In exemplary instances, step (b) comprises culturing the cells on the scaffold in vitro until cell clusters form in the pores of the scaffold and the cell clusters optionally has an average diameter which is about the same as the average diameter of the pores of the scaffold. In various aspects, step (b) comprises culturing the cells on the scaffold in vitro until cell clusters form in the pores of the scaffold and reach a size wherein the average diameter is about 250 μm to about 530 μm, optionally, about 325 μm to about 450 μm. In some aspects, step (b) comprises culturing the cells on the scaffold in vitro until cell clusters form in the pores of the scaffold and reach a size wherein the average diameter is about 470 μm±47 μm. In some aspects, step (b) comprises culturing the cells on the scaffold in vitro until cell clusters form in the pores of the scaffold and reach a size wherein the average diameter about 370 μm±37 μm. In various aspects, the scaffold comprises poly(lactide-co-glycolide) (PLG) or PEG.

In various aspects, step (b) comprises culturing the cells on the scaffold in vitro until cell clusters form in the pores of the scaffold and cells of the cell clusters express and secrete extracellular matrix (ECM) proteins within the scaffold or express at least one β-cell maturation marker (e.g., MafA, G6PC2, or PCSK1) or produce and secrete insulin at a rate greater than about 0.5 μLU per 10³ cells in response to a one-hour exposure to 28 mM glucose. Optionally step (b) comprises culturing the cells on the scaffold in vitro for about 14 to about 20 days.

The cells of the cell clusters produced by the methods of the present disclosure, in various instances, have an average diameter which is about the same as the average diameter of the pores of the scaffold after step (b). Optionally, the insulin-producing cell clusters comprise mature islet β-cells. In some instances, the method further comprises preparing the cell clusters and the scaffold for transplantation into a subject. In various aspects, the method further comprises assaying the cell clusters for expression of β cell maturation markers. In various aspects, the method further comprises assaying the cell cluster for insulin production rate in response to exposure to glucose. In various instances, the cells seeded onto the scaffold express and secrete extracellular matrix (ECM) proteins within the scaffold. In some aspects, cells seeded onto the scaffold begin to express and secrete extracellular matrix (ECM) proteins within the scaffold about 1-3 days after being seeded onto the scaffold. In various aspects, the cells seeded onto the scaffold begin to express and secrete extracellular matrix (ECM) proteins within the scaffold about 3 days after being seeded onto the scaffold. The ECM proteins comprise in some aspects, one or more of collagen IV, laminin and fibronectin in various instances. Methods of measuring ECM protein expression by cells are known in the art and described herein in EXAMPLES. In exemplary aspects, cells of the cell cluster produce and secrete insulin at a rate greater than about 0.5 μIU per 10³ cells in response to a one-hour exposure to 28 mM glucose. Optionally, the rate is greater than about 0.75 μIU per 10³ cells, greater than about 1.00 μIU per 10³ cells, greater than about 1.25 μIU per 10³ cells, or greater than about 1.30 μIU per 10³ cells. Methods of determining insulin secretion rates of cells are known in the art and described herein. See EXAMPLES. In various aspects, greater than about 85% of the seeded cells are viable for at least one week after step (a), optionally, for at least two weeks after step (a). Optionally, greater than about 90% of the seeded cells are viable for at least two weeks after the seeding step. Cell viability may be measured according to any suitable methods known in the art, at least one of which is described below in EXAMPLES.

Porous Scaffolds

With regard to the methods presently disclosed, the scaffold is porous and optionally permeable, nontoxic and/or in some aspects degradable. In exemplary embodiments, the scaffold comprises a polymeric matrix and acts as a substrate permissible for cell growth and differentiation. In exemplary aspects, the scaffold maintains residence in tissue for several weeks to years and facilitates ingrowth of tissue and the retrieval of that tissue at later time points. Such scaffolds are known in the art. See, e.g., Azarin et al., Nat Commun 6: 8094 (2015); Aguado et al., Sci Rep 5: 17566 (2015); Aguado et al., Acta Biomaterialia (2016); and Rao et al., Cancer Res 76 (18): 5209-5218 (2016); U.S. Patent Application Publication No. 2014/0072510 A1; International Patent Application Publication No. WO 2017/120486.

In various aspects, the scaffold is a synthetic polymer scaffold. In exemplary embodiments, the scaffold comprises or is manufactured with a polymer comprising or consisting of one or more of: polyamides, polycarbonates, polyalkylenes and derivatives thereof including, polyalkylene glycols, polyalkylene oxides, polyalkylene terepthalates, polymers of acrylic and methacrylic esters, including poly (methyl methacrylate), poly(ethyl methacrylate), poly (butylmethacrylate), poly(isobutyl methacrylate), poly (hexylmethacrylate), poly(isodecyl methacrylate), poly (lauryl methacrylate), poly(phenyl methacrylate), poly (methyl acrylate), poly(isopropyl acrylate), poly(isobutyl acrylate), and poly(octadecyl acrylate), polyvinyl polymers including polyvinyl alcohols, polyvinyl ethers, polyvinyl esters, polyvinyl halides, poly(vinyl acetate), and polyvinylpyrrolidone, polyglycolides, polysiloxanes, polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, and cellulose sulphate sodium salt, polypropylene, polyethylenes including poly(ethylene glycol), poly(ethylene oxide), and poly(ethylene terephthalate), and polystyrene.

In some aspects, the polymer is a biodegradable polymer, including a synthetic biodegradable polymer (e.g., polymers of lactic acid and glycolic acid, polyanhydrides, poly(ortho) esters, polyurethanes, poly(butic acid), poly(valeric acid), and poly(lactide-cocaprolactone)), and a natural biodegradable polymer (e.g., alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins (e.g., zein and other prolamines and hydrophobic proteins)), as well as any copolymer or mixture thereof. In general, these materials degrade either by enzymatic hydrolysis or exposure to water in vivo, by surface or bulk erosion.

In some aspects, the polymer is a bioadhesive polymer, such as a bioerodible hydrogel described by H. S. Sawhney, C. P. Pathak and J. A. Hubbell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

In exemplary embodiments, the polymer is a water-soluble polymer or a hydrophilic polymer. Suitable water-soluble polymers are known in the art and include, for example, polyvinylpyrrolidone, hydroxypropyl cellulose (HPC; Klucel), hydroxypropyl methylcellulose (HPMC; Methocel), nitrocellulose, hydroxypropyl ethylcellulose, hydroxypropyl butylcellulose, hydroxypropyl pentylcellulose, methyl cellulose, ethylcellulose (Ethocel), hydroxyethyl cellulose, various alkyl celluloses and hydroxyalkyl celluloses, various cellulose ethers, cellulose acetate, carboxymethyl cellulose, sodium carboxymethyl cellulose, calcium carboxymethyl cellulose, vinyl acetate/crotonic acid copolymers, poly-hydroxyalkyl methacrylate, hydroxymethyl methacrylate, methacrylic acid copolymers, polymethacrylic acid, polymethylmethacrylate, maleic anhydride/methyl vinyl ether copolymers, poly vinyl alcohol, sodium and calcium polyacrylic acid, polyacrylic acid, acidic carboxy polymers, carboxypolymethylene, carboxyvinyl polymers, polyoxyethylene polyoxypropylene copolymer, polymethylvinylether co-maleic anhydride, carboxymethylamide, potassium methacrylate divinylbenzene co-polymer, polyoxyethyleneglycols, polyethylene oxide, and derivatives, salts, and combinations thereof. In various aspects, the polymer is polyethylene glycol (PEG), polypropylene glycol, polyoxyethylated polyols (e.g., POG), polyoxyethylated sorbitol, polyoxyethylated glucose, polyoxyethylated glycerol (POG), polyoxyalkylenes, polyethylene glycol propionaldehyde, copolymers of ethylene glycol/propylene glycol, monomethoxy-polyethylene glycol, mono-(C1-C10) alkoxy- or aryloxy-polyethylene glycol, carboxymethylcellulose, polyacetals, polyvinyl alcohol (PVA), polyvinyl pyrrolidone, poly-1, 3-dioxolane, poly-1,3,6-trioxane, ethylene/maleic anhydride copolymer, poly($\beta$-amino acids) (either homopolymers or random copolymers), poly(n-vinyl pyrrolidone) polyethylene glycol, propropylene glycol homopolymers (PPG) and other polyakylene oxides, polypropylene oxide/ethylene oxide copolymers, colonic acids or other polysaccharide polymers, Ficoll or dextran and mixtures thereof. Dextrans are polysaccharide polymers of glucose subunits, predominantly linked by a1-6 linkages. Dextran is available in many molecular weight ranges, e.g., about 1 kD to about 100 kD, or from about 5, 10, 15 or 20 kD to about 20, 30, 40, 50, 60, 70, 80 or 90 kD. Linear or branched polymers are contemplated. In specific embodiments, the polymer is a polyalkylene glycol, including, for example, polyethylene glycol (PEG). Suitable scaffolds for use in the presently disclosed methods are known in the art. See, e.g., U.S. application Ser. No. 15/863,843 (which published as U.S. Patent Publication No. 20180185550 A1).

In various aspects, the average pore diameter of the scaffold used in the presently disclosed methods is about 300 $\mu$m to about 535 $\mu$m. Optionally, the average pore diameter of the scaffold used in the presently disclosed methods is about 300 $\mu$m to about 525 $\mu$m, about 300 $\mu$m to about 515 $\mu$m, about 300 $\mu$m to about 505 $\mu$m, about 300 $\mu$m to about 500 $\mu$m, about 300 $\mu$m to about 490 $\mu$m, about 300 $\mu$m to about 485 $\mu$m, about 300 $\mu$m to about 475 $\mu$m, about 300 $\mu$m to about 465 $\mu$m, about 300 $\mu$m to about 450 $\mu$m, about 300 $\mu$m to about 425 $\mu$m, about 300 $\mu$m to about 400 $\mu$m, about 300 $\mu$m to about 375 $\mu$m, about 300 $\mu$m to about 350 $\mu$m, about 300 $\mu$m to about 325 $\mu$m, about 325 $\mu$m to about 525 $\mu$m, about 300 $\mu$m to about 525 $\mu$m, about 350 $\mu$m to about 525 $\mu$m, about 375 $\mu$m to about 525 $\mu$m, about 400 $\mu$m to about 525 $\mu$m, about 425 $\mu$m to about 525 $\mu$m, about 450 $\mu$m to about 525 $\mu$m, about 465 $\mu$m to about 525 $\mu$m, about 575 $\mu$m to about 525 $\mu$m, about 485 $\mu$m to about 525 $\mu$m, about 490 $\mu$m to about 525 $\mu$m, about 500 $\mu$m to about 525 $\mu$m, about 505 $\mu$m to about 525 $\mu$m, or about 515 $\mu$m to about 525 $\mu$m. In various aspects, the scaffold is fabricated with salt porogens having an average diameter of about 250 $\mu$m to about 425 $\mu$m. In various aspects, herein the average pore diameter is about 325 $\mu$m to about 530 $\mu$m. In various aspects, the scaffold comprises polyethylene glycol and the average pore diameter is about 470 $\mu$m$\pm$47 $\mu$m. In various aspects, the scaffold comprises poly(lactide-co-glycolide) (PLG) and the average pore diameter is about 370 $\mu$m$\pm$37 $\mu$m. In various aspects, the scaffold comprises poly(ethylene glycol) (PEG) or poly(lactide-co-glycolide) (PLG), or a combination thereof. In various aspects, the scaffold is made by compression molding PLG microspheres and salt crystals. In various aspects, the scaffold is made by cast molding a mixture comprising a dissolved solution of PEG, salt crystals and a photoinitiator into a PDMS mold, followed by UV irradiation and photo-crosslinking.

In various embodiments, the scaffold is about 35 millimeters (mm) in diameter. In further embodiments, the scaffold is about or is at least about 10, 20, 25, 30, 35, 40, 45, or 50 mm in diameter. In still further embodiments, the scaffold is from about 10 to about 50, 20 to about 40, 10 to about 30, 10 to about 20, 20 to about 50, or from about 20 to about 40, or from about 20 to about 35, or from about 20 to about 30 mm in diameter. In related embodiments, the scaffold is from about 30 to about 50 or from about 30 to about 40 mm in diameter.

In some embodiments, the scaffold comprises about or at least about 500, 600, 700, 800, 900, 1000 or more islet equivalents per square centimeter (cm$^2$). In further embodiments, the scaffold comprises from about 500 to about 1000 islet equivalents per $cm^2$, or from about 500 to about 900 islet equivalents per $cm^2$, or from about 500 to about 800 islet equivalents per $cm^2$, or from about 500 to about 700 islet equivalents per $cm^2$, or from about 500 to about 600 islet equivalents per $cm^2$, or from about 700 to about 1000 islet equivalents per $cm^2$, or from about 800 to about 1000 islet equivalents per $cm^2$, or from about 900 to about 1000 islet equivalents per $cm^2$.

Compositions

The present disclosure provides a composition comprising a scaffold comprising insulin-producing cell clusters, wherein the insulin-producing cell clusters are prepared in accordance with the method of any one of the preceding claims. In various aspects, the composition comprises a pharmaceutically-acceptable carrier, diluent, or excipient and the composition in some aspects, is a pharmaceutical composition. In exemplary aspects, the composition is a pharmaceutical composition intended for administration to a human. In exemplary aspects, the composition is a sterile composition. In certain embodiments, this may be accomplished by filtration through sterile filtration membranes. The composition, in various aspects, comprises any pharmaceutically acceptable ingredient, including, for example, acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents. See, e.g., the *Handbook of Pharmaceutical Excipients*, Third Edition, A. H. Kibbe (Pharmaceutical Press, London, U K, 2000), which is incorporated by reference in its entirety. *Remington's Pharmaceutical Sciences*, Sixteenth Edition, E. W. Martin (Mack Publishing Co., Easton, Pa., 1980), which is incorporated by reference in its entirety.

Optionally, the composition is packaged in a container, e.g., a vial, a syringe, a bag, an ampoule, and the like. The container in some aspects is a ready-to-use container and optionally is for single-use.

The composition of the present disclosure can be suitable for administration by any acceptable route, including parenteral and subcutaneous administration. Other routes include intravenous, intradermal, intramuscular, intraperitoneal, intranodal and intrasplenic, for example. In various aspects, the composition is administered subcutaneously.

Methods of Treatment

Without being bound to any particular theory, the presently disclosed scaffolds comprising the insulin-producing cells clusters are useful for treating one or more insulin deficiencies and/or hyperglycemia. Accordingly, the present disclosure provides a use of the presently disclosed scaffold comprising insulin-producing cells clusters, or a composition comprising the same, for treating a subject with an insulin deficiency and/or hyperglycemia, as well as a use of the presently disclosed scaffold comprising insulin-producing cells clusters, or a composition comprising the same, in the manufacture of a medicament for treating a subject with an insulin deficiency and/or hyperglycemia. Likewise, methods of treating a subject with an insulin deficiency and/or hyperglycemia are provided by the present disclosure. In exemplary embodiments, the method comprises administering to the subject scaffold comprising insulin-producing cells clusters, or a composition comprising the same.

Similarly, the presently disclosed scaffolds comprising the insulin-producing cells clusters are useful for increasing insulin in a subject. The present disclosure also provides a use of the presently disclosed scaffold comprising insulin-producing cells clusters, or a composition comprising the same, for increasing insulin in a subject, as well as a use of the presently disclosed scaffold comprising insulin-producing cells clusters, or a composition comprising the same, in the manufacture of a medicament for increasing insulin in a subject. Methods of increasing insulin in a subject are further provided. In exemplary embodiments, the method comprises administering to the subject scaffold comprising insulin-producing cells clusters, or a composition comprising the same.

As used herein, the term "treat," as well as words related thereto, do not necessarily imply 100% or complete treatment. Rather, there are varying degrees of treatment of which one of ordinary skill in the art recognizes as having a potential benefit or therapeutic effect. In this respect, the methods of treating an insulin deficiency of the present disclosure can provide any amount or any level of treatment. Furthermore, the treatment provided by the method of the present disclosure can include treatment of one or more conditions or symptoms or signs of the insulin deficiency being treated. Signs of an insulin-deficiency include but are not limited to frequent urination, excessive thirst or hunger, Also, the treatment provided by the methods of the present disclosure can encompass slowing the progression of the insulin deficiency. In exemplary aspects, the methods treat by way of delaying the onset or recurrence of the insulin deficiency by at least 1 day, 2 days, 4 days, 6 days, 8 days, 10 days, 15 days, 30 days, two months, 3 months, 4 months, 6 months, 1 year, 2 years, 3 years, 4 years, or more. In exemplary aspects, the methods treat by way increasing the survival of the subject.

As used herein, the term "increase" and words stemming therefrom may not be a 100% or complete increase. Rather, there are varying degrees of increasing of which one of ordinary skill in the art recognizes as having a potential benefit or therapeutic effect. In exemplary embodiments, the increase provided by the methods is at least or about a 10% increase or enhancement (e.g., at least or about a 20% increase or enhancement, at least or about a 30% increase or enhancement, at least or about a 40% increase or enhancement, at least or about a 50% increase or enhancement, at least or about a 60% increase or enhancement, at least or about a 70% increase or enhancement, at least or about a 80% increase or enhancement, at least or about a 90% increase or enhancement, at least or about a 95% increase or enhancement, at least or about a 98% increase or enhancement).

In exemplary aspects, the subject of the methods of the present disclosure is a subject with diabetes, diabetes mellitus type I, diabetes mellitus type II, or gestational diabetes, either insulin-dependent or non-insulin-dependent. In some aspects, the method treats the hyperglycemic medical condition by reducing one or more complications of diabetes including nephropathy, retinopathy and vascular disease. In various aspects, the subject has an absolute deficiency of insulin secretion. In various aspects, the subject has Type I diabetes. According to *Diabetes Care*. 2009 January; 32 (Suppl 1): S62-S67. doi:10.2337/dc09-S062, individuals at increased risk of developing this type of diabetes can often be identified by serological evidence of an autoimmune pathologic process occurring in the pancreatic islets and by genetic markers. In various aspects, the subject has a relative insulin deficiency. In various instances, the subject has Type II diabetes. In various aspect, the subject is obese. In various aspects, the subject has a genetic defect of β-cell function and has maturity-onset diabetes of the young (MODY). For example, the subject has a genetic defect in Chromosome 12, HNF-1α (MODY3), a genetic defect in Chromosome 7, glucokinase (MODY2), a genetic defect in Chromosome 20, HNF-4α (MODY1), a genetic defect in Chromosome 13, insulin promoter factor (IPF-1; MODY4); a genetic defect in Chromosome 17, HNF-1β (MODY5), or a genetic defect in Chromosome 2, neuroD1 (MODY6). In exemplary aspects, the subject has a genetic defect in insulin action (e.g., Type A insulin resistance, leprechaunism, Rabson-Mendenhall Syndrome, Lipoatrophic diabetes), a disease of the exocrine pancreas (e.g., pancreatitis, trauma/pancreatectomy, neoplasia, cystic fibrosis, hemochromatosis, fibrocalculous pancreatiopathy), an endocrinopathy (e.g., acromegaly, Cushing's Syndrome, Glucagonoma, Pheochromocytoma, Hyperthyroidism, Somatostatinoma, Aldoseteronoma), a Drug- or Chemical-induced diabetes or an infection. In various aspects, the subject has pre-diabetes.

In various aspects of the methods of the present disclosure, the method comprises subcutaneously administering the composition. Optionally, the composition is administered to or within a peritoneum, omentum, or muscle of the subject. In various instances, more than one composition is administered to the subject. Optionally, two or more (e.g., 3, 4, 5, 6, 7, 8, 9, 10 or more) scaffolds comprising insulin-producing cell clusters is administered. In various aspects, the method further comprises removing the scaffold after at least about 7 days to about 150 days post-administration. In some aspects, the scaffold is removed about 7 days to 30 days to analyze in vivo development of the cell clusters within the subject. In various aspects, the scaffold is removed much later after administration to the subject, e.g., more than 2 months, more than 3-4 months, about 5-6 months after administration. In various aspects, the scaffold is not removed from the subject. In various instances, the scaffold comprises a biodegradable polymer and the scaffold is not removed from the subject.

The present disclosure provides a method of treating diabetes in a patient, the method comprising: (a) seeding pancreatic progenitor cells onto a three-dimensional, porous scaffold at a seeding density greater than about 12.5 million cells per cm³ of scaffold, wherein the scaffold comprises a plurality of pores having an average pore diameter greater than about 225 μm and less than about 600 μm; (b) culturing the pancreatic progenitor cells on the scaffold to obtain insulin-producing cell clusters within the pores of the scaffold; and (c) administering the scaffold comprising the insulin-producing cell clusters into a patient with an insulin deficiency. Optionally, steps (a) and (b) are carried out in accordance with any one of the presently disclosed methods of producing insulin-producing cell clusters. In various instances, the cells of the insulin-producing cell clusters secrete insulin at a rate greater than about 0.5 μIU per 103 cells in response to a one-hour exposure to 28 mM glucose. Optionally, cells of the insulin-producing cell clusters express at least one β-cell maturation marker during and/or after step (b). In some instances, the at least one β-cell maturation marker is MafA, G6PC2, or PCSK1.

Combinations

In various aspects, the scaffold comprising insulin-producing cells clusters, or a composition comprising the same, may be administered to the subject in combination with another anti-diabetic agent. In alternative aspects, the scaffold comprising insulin-producing cells clusters, or a composition comprising the same, may be administered to the subject in the absence of another anti-diabetic agent. The insulin may be a short-acting insulin (e.g., Humulin, Novolin), a rapid-acting insulin (e.g., NovoLog, FlexPen, Fiasp, Apidra, Humalog), an intermediate-acting insulin (e.g., Humulin N, Novolin N), long-acting insulin (e.g., Tresiba, Levemir, Lantus, Toujeo), or a combination insulin (e.g., NovoLog Mix 70/30, Humalog 75/25, Humalog 50/50, Novolin 70/30, or Ryzodeg). The anti-diabetic agent may be an amylinomimetic drug (e.g., pramlintide) or an alpha-glucosidase inhibitor (e.g., acarbose, miglitol), or biguanide (e.g., metformin or metformin combination or phenformin) or a dopamine agonist (e.g., bromocriptine) or a Dipeptidyl peptidase-4 (DPP-4) inhibitor (e.g., alogliptin, alogliptin-metformin, aloptin-pioglitazone, linagliptin, linagliptin-empagliflozin, linagliptin-metformin, saxagliptin, saxaglip-tin-metformin, sitagliptin, sitagliptin-metformin, sitagliptin and simvastatin, vildagliptin). The anti-diabetic agent in some aspects is a glucagon-like peptide or incretin mimetic, e.g., albiglutide, dulaglutide, exenatide, liraglutide, sema-glutide) or a meglitinide (e.g., nateglinide, repaglinide, repaglinide-metformin) or a (sodium-dependent glucose transporter 1 (SGLT 1) inhibitor or a sodium glucose transporter 2 (SGLT2) inhibitor (e.g., dapaglifozin, dapagliflozin-metformin, canagliflozin, canagliflozin-metformin, empagliflozin, empagliflozin-linagliptin, empagliflozin-metformin, ertugliflozin), sulfonylurea (glimepiride, glimepiride-pioglitazone, glimepiride-rosiglitazone, gliclazide, gliclazide-metformin, glipizide, glyburide, glyburide-metformin, chlorpropamide, tolazamide, tolbutamide, aceto-hexamide), or thiazolidinedione (e.g., rosiglitazone, rosiglitazone-glimepiride, rosiglitazone-metformin, piogli-tazone, pioglitazone-alogliptin, pioglitazone-glimerpiride, pioglitazone-metformin or troglitazone). In various instances, the anti-diabetic agent is leptin, Peptide YY (PYY), Pancreatic Peptide (PP), fibroblast growth factor 21 (FGF21), a Y2Y4 receptor agonist, a PPARγ inhibitor; glucokinase activators (GKA); glucagon receptor antagonist (GRA); or FBPase (fructose 1,6-bisphosphatase) inhibitor.

EXEMPLARY EMBODIMENTS

Type I diabetes (T1D), which affects an estimated 3 million Americans, is caused by autoimmune destruction of the pancreatic β-cells that results in the need for life-long insulin therapy. Although insulin therapy has been successful, hypoglycemic events and vascular complications persist [1-3]. Allogeneic islet transplantation for the treatment of T1D is a therapy in which donor islets are infused intrahepatically, which has led to the transient reversal of diabetes. However, allogeneic transplantation has several therapeutic limitations, which include a shortage of donor islets, long-term immunosuppression, and high risk of tissue rejection. All of these limitations have led to the investigation of human embryonic stem cells (hESC) as an unlimited source of functional β-cells. Multiple investigators have demonstrated the feasibility of differentiating hESC to immature β-cells in vitro and transplanting these cells to support their maturation into glucose-responsive insulin-producing β-cells [4-10]. Importantly, there are at least two major challenges with this in vitro culture and transplantation process: i) many transplants are ineffective [5, 6], indicating the need to more consistently and efficiently promote maturation of insulin-producing β-cells, and ii) transplants are typically performed at non-translatable sites, and the adaptation to clinically translatable sites reduces the efficiency of differentiation [10, 11]. Thus, there is a need for improved Type 1 diabetes treatment. There is a need for improved culturing of glucose-responsive insulin-producing β-cells.

hESC-derived β-cells have been previously shown to reverse diabetes, however more consistent and efficient methods of differentiation are required for clinical translation to treat T1D [9, 10]. Currently, state-of-the-art differentiation protocols for hESC to immature β-cells involves culture on plates or transwells at an air-liquid interface or in suspension culture [6, 9, 10].

Microporous scaffolds have been developed for extrahepatic transplantation [14-19] of murine, human, and porcine islets, which has led to engraftment and long-term function of islets that maintain euglycemia. These microporous scaffolds are herein applied to differentiate the hESC toward immature β-cells, as the microporous architecture provides the opportunity to control and support the 3D organization of cells into islet-like structures.

Three-dimensional (3D) tissue culture has been critical to derive organ-like tissue from hESC called organoids, which contain relevant tissue architecture and cellular organization [20]. Here, this approach is extended to the hESC-derived β-cells by culturing the derived pancreatic endoderm on the microporous scaffolds to promote three-dimensional growth and enhance survival prior to transplantation and function post-transplantation. Techniques described and depicted herein quantitatively assess the differentiation, maturation and function of hESC toward β-cells in vitro and in vivo [21].

The microporous scaffolds described herein have the ability to support β-cell progenitor differentiation and transplantation at a clinically translatable site at least because such scaffolds are accessible and able to support the necessary cell mass. Thus, hESC-derived pancreatic progenitors can be cultured on a porous scaffold that is subsequently transplanted in order to enhance the consistency and efficiency by which these cells develop into functional β-cells that reverse diabetes at a clinically translatable site.

In some embodiments, the microporous scaffolds include basement membrane proteins added therein or thereto. The addition of the basement membrane proteins affects the development of hESC-derived pancreatic progenitors. In one embodiment, scaffolds were coated with basement membrane proteins, such as collagen IV, laminin, or Matrigel to mimic the composition of the in vivo pancreatic ECM. Scaffolds with Matrigel coating showed significantly higher gene expression of insulin and mature β-cell markers (MAFA and PCSK1) compared to collagen IV and laminin coating. Such results indicate that an ECM cocktail of proteins contributes to the pancreatic niche environment. Cell cluster formation was promoted by optimizing the cell seeding density and scaffold pore size. Clusters formed in the scaffolds after one day and were maintained in culture for 14 days to differentiate into immature β-cells. The cells remained viable showing no signs of necrosis. Insulin and other pancreatic beta-cell-specific genes were all present in the differentiated cell clusters. Cluster size could be controlled by the dimensions of the pore of the scaffold and showed insulin expression was significantly higher when the clusters ranged from 250-425 µm compared to clusters above or below this range. Confocal imaging, was used to show that this platform allows hESCs to differentiate into complex 3D islet-like structures with glucagon and insulin-expressing cells distributed throughout the cluster.

Scaffolds seeded with the pancreatic progenitors are believed to show an increased consistency and efficiency for differentiation to immature β-cells. The scaffold design is expected to influence the fraction of insulin positive cells relative to other hormone positive cells, increase the expression of pancreatic genes associated with differentiation, and enhance activity of TFs that are associated with β-cell maturation. Scaffolds transplanted to the peritoneal fat, a clinically translatable site, should efficiently and consistently restore normoglycemia.

Thus, in some embodiments, a method of generating mature insulin-producing β-cells from stem cells, a method of restoring natural insulin production in a patient, and/or a method of treating Type 1 diabetes includes seeding a microporous polymer scaffold with pluripotent cells, such as: hPSC, iPSC, hESC, partially-differentiated β-cell progenitors, and/or pancreatic progenitors. In some embodiments, the formation of cell clusters is promoted by optimizing the cell seeding density and scaffold pore size. Various embodiments further include maintaining the cell clusters in culture on the scaffolds for a duration of time to allow for the differentiation into β-cells, immature β-cells, or β-like cell types. In some embodiments, the cells are maintained on the scaffold in vitro for 7, 14, or 21 days. In other embodiments, any suitable duration of time may be used. In various embodiments, the method further includes transplanting the scaffold into a clinically translatable location within an animal body, such as a human body. In some embodiments, the scaffold is transplanted into the peritoneal fat/cavity of a patient with Type 1 diabetes. In some embodiments, the cells on the transplanted scaffold mature into glucose-responsive insulin-producing β-cells.

In some embodiments, the polymer scaffolds comprise, consist essentially of, or consist of: PEG, PLG, PLGA, a hydrogel, or any other one or more suitable, biocompatible polymers. In some embodiments, the microporous scaffold comprises poly(ethylene glycol) (PEG) or poly(lactide-co-glycolide) (PLG). In various embodiments, the PEG is 4-arm PEG or 8-arm PEG. In further embodiments, the PEG is at least about 10, 15, 20, 25, 30, or more kilodaltons (kDa) molecular weight. In some embodiments, the scaffold further comprises one or more extracellular matrix (ECM) molecules. In some embodiments, the ECM molecule is collagen, laminin, or fibronectin. In further embodiments, a combination of extracellular matrix molecules is utilized. In some embodiments, a scaffold of the disclosure comprises collagen and laminin, collagen and fibronectin, and/or laminin and fibronectin. In further embodiments, the scaffold comprises collagen and laminin. In some embodiments, the polymer scaffolds have pore sizes ranging from 250-425 µm. In some embodiments, a scaffold having one or more of the properties described in U.S. application Ser. No. 15/863,843 is used, the disclosure of which is herein incorporated by reference in its entirety.

The following examples are given merely to illustrate the present invention and not in any way to limit its scope.

EXAMPLES

The following examples collectively demonstrate the development of a 3D niche microenvironment to improve stem cell-derived β-cell maturation for the treatment of Type I diabetes.

The current challenges of using hESC-derived β-cells for the treatment of diabetes include a lack of efficient ways for achieving homogenous maturation or differentiation, cell loss occurring during and after transplantation of clusters into a patient, and defining and understanding the in vivo niche required for maturation. A microporous scaffold culture was proposed for producing islet-like tissue on the scaffold. Here, it is postulated that such scaffold cultures offer improvements over known air-liquid interface cultures and suspension cultures.

In the studies presented herein, scaffold pore size, cell seeding density, and the requirement for ECM proteins coated onto scaffolds is analyzed. PLG scaffolds or PEG scaffolds were fabricated. PLG scaffolds were selected for fabrication, because they have a tunable biodegradation, stiff mechanical properties, hydrophobic, and good cell attachment properties. PEG scaffolds were selected for fabrication because they are non-degradable, elastic, tissue-like mechanical properties, and hydrophilic. It was found that scaffold pore size influences the cluster size during hESC differentiation. It was also found that β-cell cluster formation in porous hESC scaffold cultures is dependent on cell seeding densities. Large clusters (e.g., 250 μm to 425 μm) enhanced pancreatic expression of immature hESC derived β-cells for insulin, glucagon, MafA, PDX1 and NKx6.1, compared to small clusters (60-106 μm) and medium clusters (106-250 μm). Clusters larger than 425 μm (e.g., 500-600 μm) showed similar enhancements as the large clusters though not as robust. It was demonstrated that increased cell-cell interactions promote β-cell maturation, cluster formation in scaffold culture is important for β-cell maturation, and large clusters maximize the influence of pancreatic cell-cell interactions. It was shown that scaffold cultures reduced the need for providing a complex ECM environment for β-cell maturation. Non-ECM coated scaffolds showed similar influence as Matrigel-coated scaffolds for in vitro β-cell maturation. It was shown that the seeded cells secreted ECM molecules and established a pancreatic niche on scaffolds. In vitro scaffold cultures allow hESC-derived β-cells to dynamically remodel the niche environment with ECM proteins (e.g., collagen IV, laminin). We demonstrated that manipulating cell matrix interactions can enhance β-cell maturation, and non-ECM coated scaffold cultures allow hESC-derived β-cells to dynamically remodel their niche. Taken together, microporous scaffolds provide a comparable platform for in vitro 3D hESC β-cell cultures. A cluster heterogeneity analysis showed that clusters on scaffold cultures have a similar transcription profile (involving e.g., MafA, Nkx6.1, glucagon, insulin, ECAD, PDX1, PCSK1). It was also demonstrated that hESC-derived β-cells exhibit in vivo maturation on scaffold cultures. Euglycemia could be restored on microporous scaffolds using suspension clusters. Optimizing hESC differentiation helps β-cell maturation on scaffold cultures align with Melton clusters. In conclusion, scaffold cultures can provide a platform that will enhance the efficiency which cells develop into functional β-cells.

Example 1

This example describes exemplary methods of fabricating scaffolds suitable for use in the presently disclosed method of preparing insulin-producing cell clusters.

Two types of scaffolds were used in the studies described below: poly(lactide-co-glycolide) (PLG) scaffolds and polyethylene glycol (PEG) scaffolds. Scaffolds were fabricated as previously described [Kasputis et al., ACS Biomater. Sci. Eng. 4 (2018) 1770-1778. doi:10.1021/ acsbiomaterials.7b00912; and Rios et al., Biotechnol. Bioeng. 115 (2018) 2356-2364. doi:10.1002/bit.26741]. Briefly, PLG microporous scaffolds were fabricated by compression molding PLG microspheres (75:25 mole ratio D,L-lactide to glycolide) and micron-sized salt crystals in a 1:30 ratio of PLG microspheres to salt. The mixture was humidified in an incubator for 7 min and then thoroughly mixed again. Scaffolds were compression molded with 77.5 mg of polymer-salt mixture into cylinders 5 mm in diameter by 2 mm in height using a 5 mm KBr die (International Crystal Laboratories, Garfield, NJ) at 1500 psi for 45s. Molded constructs were gas foamed in 800 psi carbon dioxide for 16 h in a pressure vessel. The vessel was depressurized at a controlled rate for 30 min. On the day of cell seeding, scaffolds were leached in water for 1.5 h, changing the water once after 1 h. Scaffolds were disinfected by submersion in 70% ethanol for 30 seconds and rinsed multiple times with phosphate buffer solution (PBS).

For the PEG hydrogel scaffolds, PEG-maleimide (4-arm, molecular weight 20 kDA, 20% wt/wt) polymer was dissolved in a HEPES buffer solution, mixed with NaCl crystals and a photoinitiator (Irgacure-2959) then cast into a polymethylsiloxane (PDMS) mold (diameter: 5 mm, thickness 2 mm). The solution was irradiated with UV light to photocrosslink the PEG-maleimide and then washed to remove the sodium chloride and unreacted photoinitiator. The pore size of the scaffolds can be readily controlled through the dimensions of the porogen, and scaffold pore sizes using porogens of 63 to 108 μm, 108 to 225 μm, 225 to 450 μm, and 500 to 600 μm were investigated.

Example 2

This example describes an exemplary in vitro method of differentiating stem cells to pancreatic progenitor cells.

The H1 human embryonic stem cell (hESC) line used for these studies was obtained from the WiCell Research Institute (Madison, WI). These pluripotent cells were maintained on Matrigel (BD Biosciences, San Jose, CA) in mTeSR1 medium (STEMCELL Technologies, Vancouver, Canada). When ~80% confluent (~3-4 days after plating), cells were passaged using Gentle Cell Disassociation Reagent (STEMCELL Technologies).

The differentiation of H1 hESC line (Stage 0; S0) to pancreatic progenitor cells (Stage 4 (S4)) were performed as essentially described in Rezania et al., Nat Biotechnol 32:1121-1133 (2014). Briefly, to obtain Stage 1 (S1) definitive endoderm cells, a 3-day procedure was followed that began with rinsing undifferentiated pluripotent stem cells (S0 cells of the H1 hESC line) plated on 1:30 Matrigel-coated surfaces with a first medium comprising 1×DPBS without $Mg^{2+}$ and $Ca^{2+}$ and then exposing the rinsed cells to a second medium. The second medium was made by supplementing MCDB 131 medium (Life, Cat #10372-019) with 1.5 g/l sodium bicarbonate (Sigma, MO, Cat #S6297), 1× Glutamax (Life, Cat #35050-079), 10 mM final glucose (Sigma, Cat #G8769) concentration, 0.5% BSA (fatty acid free BSA, Proliant, IA, Cat #68700), 100 ng/ml GDF8 (Pepro-Tech; Rocky Hill, NJ, Cat #120-00), and 1 mM of MCX-928 (GSK3b inhibitor[3], Janssen). On the second day of the 3-day procedure (Day 2), cells were cultured in MCDB along with 0.5% BSA, 1.5 g/l sodium bicarbonate, 1× Glutamax, 10 mM glucose, 100 ng/ml GDF8 and 0.1 mM of MCX-928. On the third day of the 3-day procedure (Day 3), cells were cultured in MCDB containing 0.5% BSA, 1.5 g/l sodium bicarbonate, 1× Glutamax, 10 mM glucose and 100 ng/ml GDF8. S1 cells were obtained upon completion of this procedure.

In order to obtain Stage 2 (S2) primitive gut tube cells, a 2-day procedure was carried out, which began with rinsing S1 cells with 1×DPBS (without Mg$^{2+}$ and Ca$^{2+}$). Following the rinse step, cells were exposed to MCDB 131 medium supplemented with 1.5 g/l sodium bicarbonate, 1× Glutamax, 10 mM final glucose concentration, 0.5% BSA, 0.25 mM ascorbic acid (Sigma, Cat #A4544) and 50 ng/ml of FGF7 (R & D Systems, Cat #251-KG) for 2 days. During this stage, media was changed daily to fresh media of the same composition. S2 cells were obtained upon completion of these steps.

Stage 3 (S3) posterior foregut cells were obtained upon a 2-day procedure, during which S2 cells were cultured for two days in MCDB 131 medium supplemented with 2.5 g/l sodium bicarbonate, 1× Glutamax, 10 mM final glucose concentration, 2% BSA, 0.25 mM ascorbic acid, 50 ng/ml of FGF7, 0.25 mM SANT-1 (Sigma, Cat #S4572), 1 mM retinoic acid (RA; Sigma, Cat #R2625), 100 nM LDN193189 (LDN; BMP receptor inhibitor, Stemgent, CA, Cat #04-0019), 1:200 ITS-X (Life, Cat #51500056), and 200 nM TPB (PKC activator, custom synthesis, ChemPartner, China).

Stage 4 (S4) pancreatic endoderm cells expressing PDX1 and NKX6.1 were obtained by following a 3-day procedure, during which S3 cells were exposed to MCDB 131 medium supplemented with 2.5 g/l sodium bicarbonate, 1× Glutamax, 10 mM final glucose concentration, 2% BSA, 0.25 mM ascorbic acid, 2 ng/ml of FGF7, 0.25 mM SANT-1, 0.1 mM retinoic acid, 200 nM LDN193189, 1:200 ITS-X, and 100 nM TPB. The S3 cells were cultured in this medium for 3 days. S4 cells were obtained at the end of the 3 days.

For each of the stages (S0→S1, S1→S2, S2→S3, and S3→S4), the cultures were fed every day, unless specified otherwise. Once obtained, S4 cells may be treated for 4 h with 10 mM Y-27632 and then rinsed with 1×DPBS without Mg$^{2+}$ and Ca$^{2+}$, followed by exposure to TrypLE (1×) for 3-5 min at room temperature. Such treatment led to released, dissociated cells that could then be washed with basal BLAR medium or MCDB 131 medium.

A culture of S4 cells may be established as an air-liquid interface culture, as described in Rezania et al., Nat Biotechnol 32:1121-1133 (2014), wherein washed S4 cells are spun for 3 min at 1,000 r.p.m. and the resulting S4 cell pellet are resuspended as single cells at a density of ~0.5×10$^5$ cells/ml on filter inserts (BD, Cat #35-3493 or Corning Cat #3420); 5-10 ml per spot for a total of 0.25-0.5×10$^6$ cells/spot) at an air-liquid interface. Cultures are generally fed every day.

Alternatively, S4 cells may be cultured on a three-dimensional scaffold as described in Example 3.

Example 3

This example describes an exemplary in vitro method of preparing insulin-producing cell clusters for transplantation into a subject. In this exemplary method, the growth and differentiation of pancreatic progenitor cells are carried out on a three-dimensional, porous scaffold to arrive at β-cell clusters comprising glucose-responsive, insulin-producing cells.

The purpose of this study was to determine whether microporous scaffolds could function as a support assembly for differentiation of pancreatic progenitor cells into β-cell clusters. Herein, microporous polymer scaffolds served as an in vitro platform for the efficient differentiation of hPSC-derived pancreatic progenitor cells to insulin-producing glucose-responsive β-cells. These scaffold cultures were an alternative to the suspension cultures described above in Example 2 and in Rezania et al., Nat Biotechnol 32:1121-1133 (2014).

To initiate an in vitro scaffold culture (also referred to herein as "on-scaffold culture) for cell differentiation of pancreatic progenitor cells to insulin-producing glucose-responsive β-cells (differentiation of Stage 4 cells to Stage 5 cells and further differentiation of Stage 5 cells to Stage 6 cells), scaffolds formed from the synthetic polymeric materials, PLG or PEG, were fabricated as described in Example 1. Prior to cell seeding, scaffolds were washed in cell media solution then briefly dried on sterile gauze for 15-30 seconds to improve the absorption of the cell solution into the scaffold. Scaffolds that were not dehydrated in this manner remained over-saturated with solution, thus, the cell suspension will spill out of the scaffold and interfere with the absorption of the cell solution into the scaffold. Additionally, this scaffold dehydration process advantageously prevented over-drying the scaffolds, which, in certain instances, such as when hydrophobic PLG scaffolds were used, could cause surface tension on the scaffold to be too great to allow the liquid to enter the scaffold. This would then lead to reduced absorption of the cell solution into the scaffold. On the first day of stage 5 (S5), S4 pancreatic progenitor cells, e.g., those obtained via the process described in Example 2, were dispersed into single-cells using TrypLE™ Express (Life Technologies) prior to being seeded onto dried scaffolds. TrypLE™ Express was tested alongside other dissociation buffers, including gentle cell dissociation reagent, Accutase, and trypsin, and TrypLE™ Express and trypsin were found to yield the highest number of viable single cells after treatment, whereas treatment with the other dissociation buffers did not dissociate cells enough or led to higher cell death. The use of TrypLE™ Express efficiently dissociated S4 cells into single cells, which contributed to a more uniform distribution of cells compared to S4 cells in small aggregates. After treatment of S4 cells with TrypLE™ Express, S4 cells were washed with S5 basal media and centrifuged at 300 rcf for 5 min and subsequently resuspended in 10 ml of S5 basal media. The volume of cell solution seeded on the scaffold was less than 30 μL as this was the maximum volume the scaffold could retain before reaching a saturation point where cells would spill out of the scaffold. In order to ensure the seeding volume was less then 30 μL, a cell count was performed and the cell suspension was aliquoted into 1.5 mL microcentrifuge tubes with each tube containing the number of cells needed to seed one scaffold. The small aliquoted volumes were then re-centrifuged to create a cell pellet of S4 cells and the supernatant solution was removed so that a 20-25 μl volume remained. S4 cells were then re-suspended in the reduced volume using a pipet and seeded on both faces of the scaffolds at varying seeding densities ranging from 12.5 million cells/cm$^3$ to 250 million cells/cm$^3$ of scaffold. Seeding densities included 12.5 million cells/cm$^3$, 125 million cells/cm$^3$ and 250 million cells/cm$^3$. After the seeding step, the scaffolds were incubated for 10 min to allow the cell solution to be further absorbed into the scaffold. It was found that distributing cells across both faces of the scaffold led to higher numbers of cells reaching the interior pores of the scaffold, compared to distributing cells across only one face of the scaffold.

As a control, a traditional suspension culture was maintained per the described protocol Rezania et al., Nat Biotechnol 32:1121-1133 (2014). Briefly, undifferentiated hPSCs were initially seeded at 1.0 million cells/mL in ultra-low attachment 6 well plates (Corning, VWR), placed on an Orbi-Shaker (Benchmark), and set at rotation rate of 95 rpm in a 37° C. incubator, 5% CO2, and 100% humidity. Cells were cultured for 48 hr in mTeSR1 and then cultured in the differentiation media. Human islets were acquired from Cell Trans Inc. for comparison.

Scaffold and control suspension cultures were maintained for 1-2 weeks according to the protocols described below to support differentiation of the seeded S4 cells to S5 cells and finally to S6 cells.

The scaffolds comprising the seeded S4 cells were housed on a transwell membrane in 6-well plates. The plane of the membrane aligned with the air-liquid interface cell culture system in Stage 5 (S5) media for 3 days to obtain S5 pancreatic endocrine precursor cells that were PDX1$^+$/NKX6.1$^+$/NEUROD1$^+$. S5 medium comprised of MDCB 131 medium supplemented with 1.5 g/l sodium bicarbonate, 1× Glutamax, 20 mM final glucose concentration, 2% BSA, 0.25 mM SANT-1, 0.05 mM retinoic acid, 100 nM LDN193189, 1:200 ITS-X, 1 mM T3 (3,3',5-Triiodo-I-thyronine sodium salt, Sigma, T6397), 10 mM ALK5 inhibitor II (Enzo Life Sciences, NY, Cat #ALX-270-445), 10 mM zinc sulfate (Sigma, Z0251) and 10 mg/ml of heparin (Sigma, H3149).

S5 cells were cultured in Stage 6 (S6) medium for 7-11 days. S6 medium comprised MCDB 131 medium supplemented with 1.5 g/l sodium bicarbonate, 1× Glutamax, 20 mM final glucose concentration, 2% BSA, 100 nM LDN193189, 1:200 ITS-X, 1 mM T3, 10 mM ALK5 inhibitor II, 10 mM zinc sulfate, 100 nM gamma secretase inhibitor XX (EMD MilliPore, MA, Cat #565789). Following the 7 days of being cultured in S6 medium, the cells were exposed to S6 medium supplemented with heparin (10 mg/ml) for an additional 1-8 days to obtain S6 NKX6.1$^+$/insulin$^+$ cells. The process of obtaining S6 cells from S5 cells took about 7 days in total.

At the end of the 1-2 weeks, the cell clusters on the scaffolds were evaluated and compared to those of the control suspension culture. As shown in FIG. 1A, the PLG scaffold and PEG scaffold provided a similar microporous structure allowing for the establishment of an in vitro scaffold culture of pancreatic progenitors to β-cells, though each material type offered distinct material properties that can distinguish the role of structure relative to the role of the material. Cluster formation within the microporous scaffold cultures is shown in FIG. 1B and the traditional suspension culture is shown in FIG. 1C.

The effects of seeding density were evaluated by seeding at 12.5 million cells/cm$^3$, 125 million cells/cm$^3$ and 250 million cells/cm$^3$. hPSC-derived pancreatic progenitors dissociated into single cells were initially seeded onto microporous scaffolds at a density of 12.5 million cells/cm$^3$ for culture. The use of single cells allows the proper infiltration of cells into the pores of the scaffolds while providing relatively uninhibited access of media to the cells. Through confocal microscopy, it was found that this seeding density was not sufficient for cluster formation to occur as cells were localized to the surface of the pores (FIG. 1D). Increasing the seeding density 10-fold to 125 million cells/cm$^3$ resulted in the cells assembling into 3D clusters within one day after seeding (FIG. 1E), which resembles the self-organization that occurs in suspension cultures. Cell viability was consistently high (>90%) throughout the 14-day experiment for both PEG and PLG scaffold conditions (FIG. 1F-K). These observations indicated that the assembly of cells into clusters could be supported within the micropores yet was dependent on the cell density. This high cell seeding density resulted in a uniform distribution of cells and clusters throughout the scaffold (FIG. 1L-N). At densities greater than 125 million cells/cm$^3$, cells began to clump on the surface.

The cell clusters were then tested for differentiation towards insulin-producing glucose-responsive β-cells (Stages 5-6) by assaying the cell clusters for expression of β cell maturation markers (Example 4) and insulin production rate in response to exposure to glucose (Example 6).

Example 4

This example describes the maturation of β-cell clusters within scaffolds and an investigation to determine the impact pore size has on the ability to form clusters of distinct sizes. The cell structures within the pores of the scaffold were analyzed by histology and gene expression.

The feasibility of generating β-cell clusters in microporous scaffolds was investigated by measuring the expression of β-cell marker genes, which were compared with cells generated in suspension culture and human islets. Using qRT-PCR analysis, it was found cells cultured within PEG and PLG scaffolds had an increased expression level of the endocrine hormone marker gene for insulin relative to Stage 4 pancreatic progenitors. Additionally, β-cell maturation markers (MafA, G6PC2, and PCSK1) had expression levels on scaffold cultures that were at least comparable to suspension culture controls if not significantly increased.

On average, the suspension culture produced clusters around 234±63 μm in diameter (n=48 individual clusters). The tunable design of the scaffold pores was used to assess how varying the cluster size would influence maturation within the scaffold. A correlation between scaffold pore sizes and the expression of key β-cell markers was observed with larger pore sizes promoting higher expression levels. For PEG scaffolds, pore sizes in the range of 250-425 μm had increased expression of pancreatic transcription factors (PDX1 and Nkx6.1) compared to suspension and scaffolds with pore size smaller than 250 μm (FIG. 2A). The expression of Nkx6.1 was lower than human islets for both suspension and scaffold conditions suggesting the cells have not fully matured. However, the expression of insulin had a significant increase on scaffolds with pore sizes of 250-425 μm compared to suspension clusters and the other scaffold conditions. This trend between scaffold pore size and cell development was observed in the expression of β-cell maturation markers as well. Scaffolds with a pore size of 250-425 μm resulted in the highest expression of the insulin gene transcription factor, MafA, with the 500-600 μm pore size scaffolds exhibiting the second highest expression out of the in vitro conditions. The maturation marker proprotein convertase 1 (PCSK1) is one of the key enzymes associated with insulin processing and showed expression levels to be higher in scaffold cultures with 250-425 μm pore sizes compared to the scaffolds with smaller pore sizes as well as suspension clusters. hPSC-derived pancreatic progenitors cultured on PLG scaffolds similarly demonstrated the development of β-cells with maturation showing a correlation with pore size (FIG. 2B). Insulin expression for PLG scaffold cultures with 250-425 μm pore sizes was significantly increased relative to the pancreatic progenitors. The expression of pancreatic β-cell transcription factor PDX1 and Nkx6.1 in all four PLG scaffold conditions were lower than human islets but comparable to suspension clusters. While this suggests maturation could be improved, PLG scaffolds with 250-425 μm pore sizes showed increased expression in the key maturation marker, G6PC2, relative to pancreatic progenitors and suspension clusters. Overall, cells cultured in PEG and PLG microporous scaffolds generally showed increased expression levels of β-cell maturation markers. While the maturation was still not comparable to human islets, this deficit relative to islets is to be expected as, per the protocol used, in vivo transplantation is necessary to reach full maturation.

This analysis revealed that pancreatic progenitors differentiated to β-cells in the PLG and PEG microporous scaffold show, at a minimum, comparable gene expression levels to the traditional suspension culture. The observations also identified a relationship between scaffold pore size and β-cell maturation with 250-425 μm pore size showing more significant improvements in β-cell development than in suspension culture. Since this pore size measurement was based on the salt porogen size used during fabrication, measurements after the scaffolds had been exposed to media were also performed. Using imaging analysis, the pore size distribution for PLG and PEG scaffold cultures fabricated with 250-425 μm salt porogens were determined as 371±33 μm (n=30 individual pores) and 468±62 μm (n=32 individual pores), respectively, after 24 hours in cell media. The pore size for wet PLG scaffolds remained within the estimated range while wet PEG gels had an average pore size distribution slightly above the range, likely due to swelling. Overall, based on these findings, the following studies focused on scaffolds with a relative pore size of 250-425 μm.

Example 5

This example describes the cell-cell communication in microporous scaffold cultures during β-cell maturation.

The cell-cell interactions within the scaffold culture that drive maturation in the pancreatic niche environment were investigated next. The cell surface adhesion protein epithelial cadherin (ECAD) plays a critical role in the development of islets and intra-islet communication and is implicated in efficient insulin secretion from β-cells [Rogers et al., Cell. Physiol. Biochem. 20 (2007) 987-994. doi:10.1159/000110459; Jacques et al., Endocrinology. 149 (2008) 2494-2505. doi:10.1210/en.2007-0974, Carvell et al., Cell. Physiol. Biochem. Int. J. Exp. Cell. Physiol. Biochem. Pharmacol. 20 (2007) 617-626. doi:10.1159/000107545, and Wakae-Takada et al., Diabetologia. 56 (2013) 856-866. doi:10.1007/s00125-012-2824-6]. Thus, the presence of ECAD was assessed through qRT-PCR analysis in both scaffold cultures and suspension clusters. ECAD gene expression levels were increased in cells cultured in PLG microporous scaffolds compared to suspension clusters (3.05±1.21 vs 0.57±0.03, n=4, P<0.05). (FIG. 3A). PEG scaffold cultures showed comparable levels of ECAD expression relative to suspension clusters (2.80±0.96 vs 0.57±0.03, n=3-4). Cell-cell interactions were further investigated through immunostaining where E-cadherin was shown to be localized in small regions in the interior of the suspension clusters with increased co-expression with insulin-positive cells around the exterior of the clusters (FIG. 3B). Alternatively, in PLG scaffold cultures, ECAD was distributed throughout the interior of the clusters and with co-expressed insulin-positive cells (FIG. 3C). Imaging analysis of DAPI$^+$ cells expressing ECAD per the total area confirmed PLG scaffold cultures significantly increased protein expression of ECAD compared to suspension (42%±5 vs 21%±4 of total cell population, n=4; P<0.01). Our data suggests that microporous scaffold cultures, particularly PLG, promote cell-cell interactions that can play a role in driving β-cell maturation.

Example 6

This example demonstrates the hPSC-derived β-cell glucose-responsive in vitro function within microporous scaffolds.

Figure 4A:
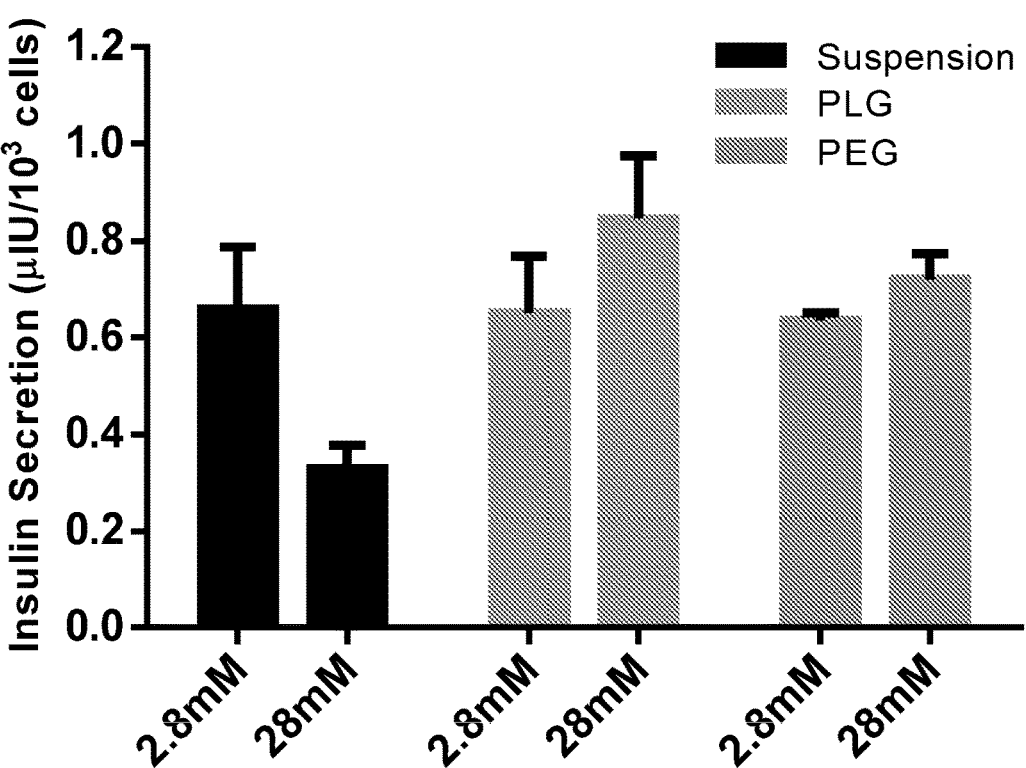
FIGS. 4A-4B demonstrate the efficient generation of glucose-responsive B-Cells from human pancreatic progenitors differentiated on microporous scaffold cultures. Human insulin secretion from PLG and PEG scaffold cultures and suspension clusters in response to low and high glucose concentrations under static conditions (scaffold cultures: n=4 biological replicates, suspension: n=5 biological replicates).
Figure 4B:
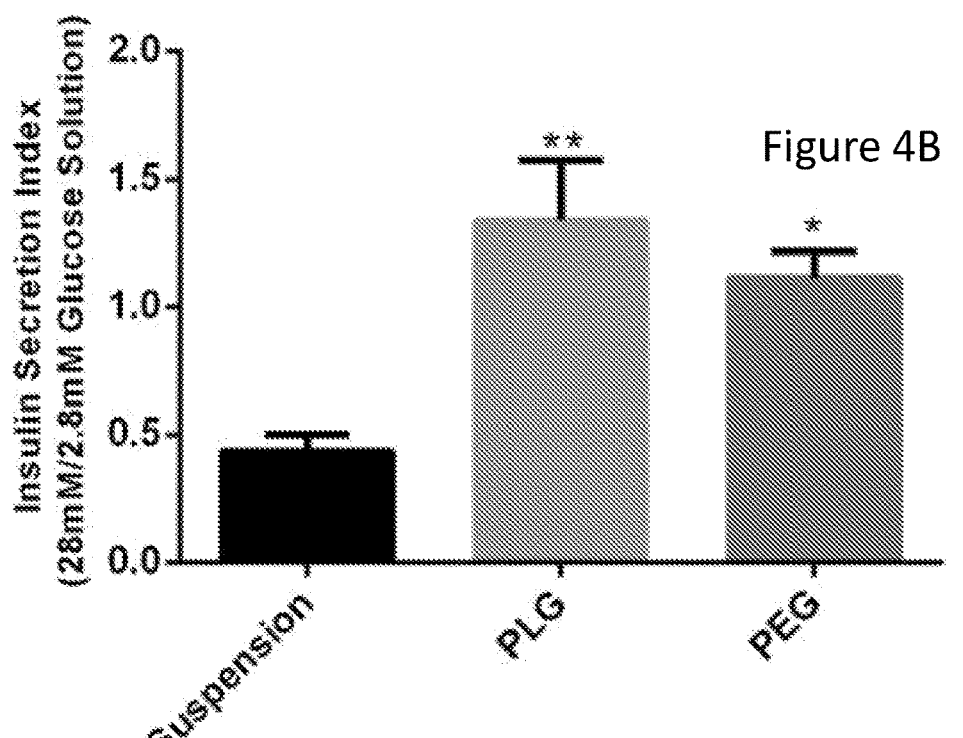

The function of these β-cell clusters in scaffolds was next examined by measuring their ability to secrete insulin in a glucose-responsive manner through a GSIS assay. Scaffold cultures and suspension clusters at the end of the six-stage differentiation were exposed to 2.8 mM and 28 mM glucose solutions, respectively. At the low glucose concentration, the cells in suspension or on scaffolds secreted similar quantities of insulin (FIG. 4A). At the high glucose concentration, an increase in insulin secretion per cell from both the PLG and PEG scaffold cultures, averaging 0.84±0.23 and 0.72±0.10 μIU/$10^3$ cells, respectively, was observed. Whereas the suspension clusters in a high glucose solution secreted low amounts of insulin, 0.33±0.10 μIU/$10^3$ cells, and were not glucose responsive. hPSC-derived β-cells cultured on the PLG scaffold had the highest insulin secretion index, with a threefold increase compared to the suspension culture control (1.34±0.20 vs 0.43±0.06, n=3, P<0.01) (FIG. 4B). PEG scaffold cultures also showed higher insulin secretion compared to the suspension control (1.11±0.09, n=3, P<0.05) yet lower insulin secretion than PLG. It is important to note that while the β-cells on scaffold cultures demonstrate a capacity for glucose-stimulated insulin secretion, the magnitude of response suggests these cells may not be the same as fully mature functional β-cells. Since the PLG scaffold demonstrated increased ECAD expression, had a higher degree of function, and is better for protein adsorption compared to PEG [Michel et al., Langmuir. 21 (2005) 12327-12332. doi:10.1021/la051726h; and Jeong et al., Colloids Surf. B Biointerfaces. 18 (2000) 371-379. doi:10.1016/S0927-7765 (99) 00162-9], subsequent studies employed this material for further investigation of the matrix environment supporting β-cell maturation.

Example 7

This example demonstrates the ECM deposition by hPSC-derived β-cell clusters and the β-cell maturation on ECM-modified microporous scaffolds.

Figures 5A, 5B, 5C, 5D, 5E, 5F, 5G:
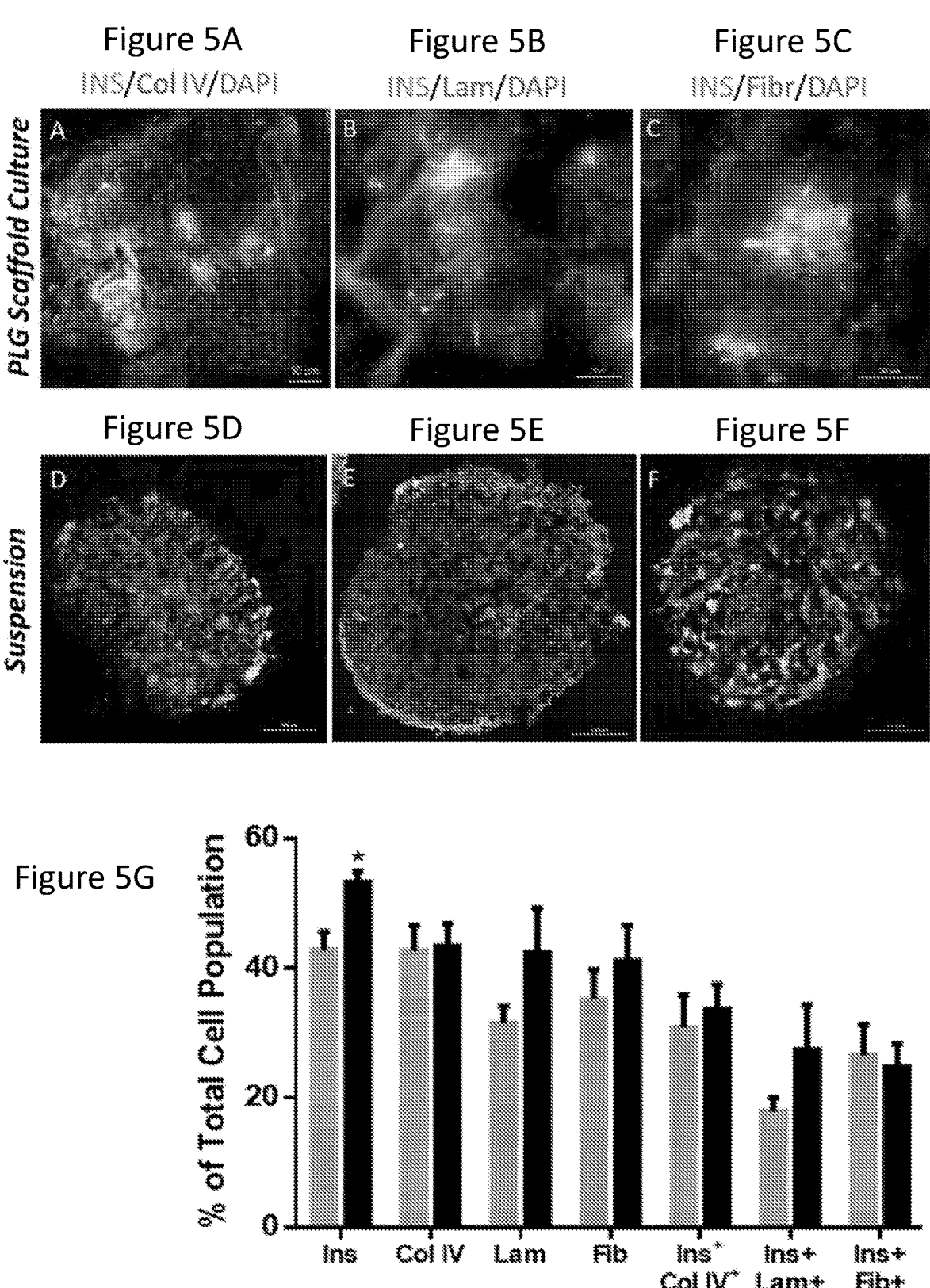
FIGS. 5A-5G demonstrate that scaffold cultures permit hPSC-derived β-cell-secreted ECM deposition. Matrix composition surrounding β-cells is shown by representative immunofluorescent staining of PLG scaffold culture (FIGS. 5A-5C) and suspension cluster (FIGS. 5D-5F) for insulin (INS; green), ECM protein (collagen IV (Col IV), laminin (Lam), or fibronectin (Fibr)) (red) and DAPI (blue). Immuno-histological analysis was performed using the percentage of DAPI$^+$ cells expressing insulin, ECM proteins and cells colocalized with insulin and ECM proteins in suspension (gray) and PLG microporous scaffolds (black) (*$P \leq 0.05$ compared to suspension, n=4 biological replicates) with error bars representing SEM and the graph of the % of Total Cell Population is shown in FIG. 5G.

The ECM within the cultured cells was subsequently assessed, as ECM basement membrane proteins are a critical component of the pancreatic environment supporting islets. Since cells cultured on PLG scaffolds showed signs of β-like development and function, immunofluorescence analysis was used to investigate if the cells were establishing a matrix similar to the pancreas within the scaffold. The presence of insulin-positive cells within the clusters were first evaluated to confirm the pancreatic progenitors were developing into β-like cells. An increase in insulin-expression of DAPI$^+$ cells in PLG scaffold cultures (FIG. 5A-C) compared to suspension cultures (FIG. 5D-F) (53%±2 vs 44%±3, n=4, P≤0.05) was observed. The results also showed ECM proteins commonly found in the extracellular matrix surrounding islets, i.e. collagen IV, laminin and fibronectin, were present in both suspension and scaffold cultures. Imaging analysis confirmed that the percentage of DAPI$^+$ cells localized to ECM protein expression in the PLG scaffold cultures was comparable to suspension (collagen IV: 44%±4 vs 43%±4; n=4; laminin: 42%±6 vs 31%±3, n=4; fibronectin:

41%±5 vs 35%±5, n=4) (FIG. 5G). ECM protein was uniformly distributed across the cell cluster in both conditions as well. Thus, relative to suspension cultures, the scaffold provides a similar supportive matrix for β-cell clusters that consists of ECM proteins commonly found in the pancreas tissue.

Figure 6A:
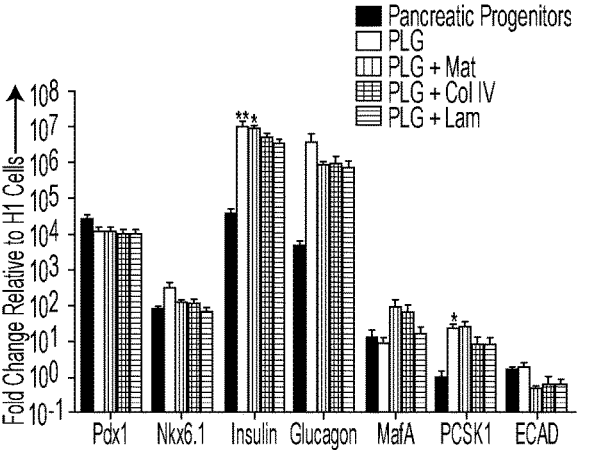
FIGS. 6A-6D show the effects of ECM-modified scaffold cultures on pancreatic progenitor differentiation. A graph of pancreatic gene expression profile of pancreatic progenitor cells cultured on ECM-coated microporous PLG scaffolds (*$P \leq 0.05$, $P \leq 0.005$ versus pancreatic progenitors using one-way ANOVA with Dunnett test for multiple comparisons, n=4 biological replicates for all genes) is shown in FIG. 6A**. A graph of gene expression for CollVA1 and LamA5 of Stage 6 β-cells (*$P \leq 0.05$ compared to human islets using student t-test comparisons, n=4 biological replicates for all genes) is shown in FIG. 6B. A graph of human insulin secretion in response to low and high glucose concentrations from PLG scaffold cultures coated with either Matrigel (Mat), laminin (Lam) or collagen IV (Col IV) under static conditions and compared to a non-coated PLG scaffold as a control (n=3 biological replicates) is shown in FIG. 6C. A graph of the stimulation index (calculated as the ratio of insulin release in high to low glucose concentrations) is shown in FIG. 6D. Error bars represent the SEM.
Figure 6B:
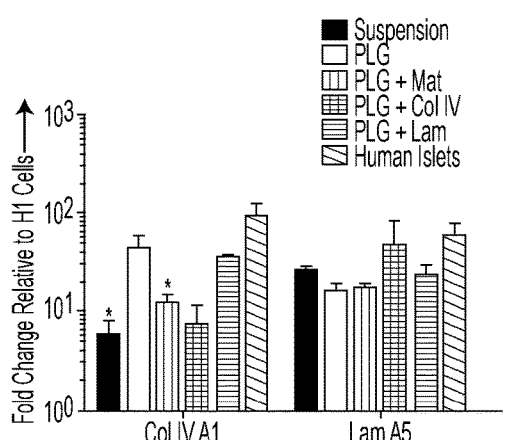
Figure 6C:
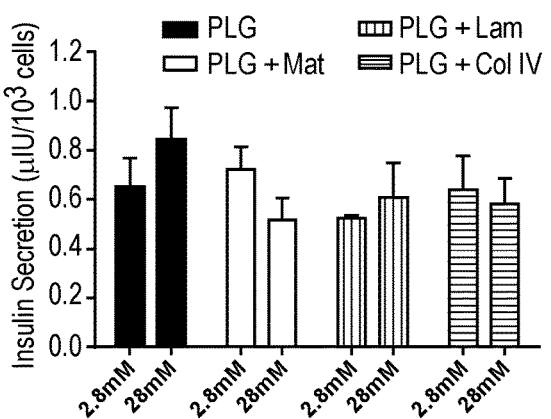
Figure 6D:
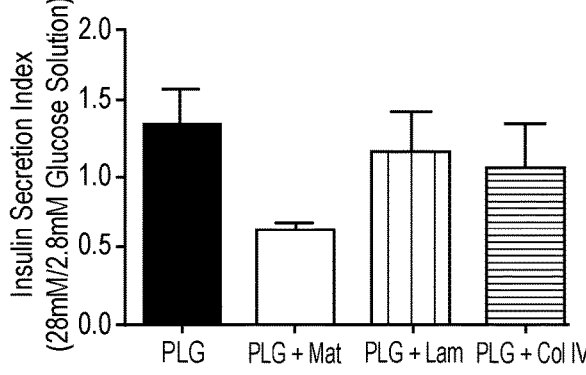

The presence of ECM protein deposition on the naked scaffold motivated studies in which ECM proteins commonly found in the pancreas were deposited on the scaffold prior to cell seeding as a means to further enhance maturation. Using qRT-PCR analysis, pancreatic progenitor maturation to β-cells on PLG scaffolds coated with either collagen IV, laminin or Matrigel was investigated. Naked microporous scaffolds and scaffolds coated with ECM proteins showed comparable levels of expression for endocrine transcription factors (PDX1 and Nkx6.1) (FIG. 6A). However, only naked scaffolds and Matrigel coated scaffolds exhibited an increase in insulin expression relative to pancreatic progenitors. Evaluating cell maturation on the scaffolds also showed that, relative to pancreatic progenitors, only the naked scaffold cultures enhanced the expression of PCSK1. An analysis of the expression of pancreatic-related ECM genes demonstrated that the expression of COL4A1 gene, coding for collagen type IV, in naked scaffolds as well as scaffolds coated with collagen IV and laminin was comparable to human islets. However, a decrease of COL4A1 gene expression was observed in suspension cultures and scaffolds coated with Matrigel (FIG. 6B). Laminin production, indicated by LamA5 gene, was observed to be comparable to human islets across all culture conditions. Finally, cell maturation through glucose-responsive function was assessed. At the low glucose concentration, the cells on ECM-coated scaffolds and naked scaffolds secreted similar quantities of insulin (FIG. 6C). However, for the high glucose concentration, insulin secretion per cell increased for only the laminin-coated PLG and naked scaffold cultures, averaging $0.61\pm0.24$ and $0.84\pm0.23$ $\mu IU/10^3$ cells, respectively. Interestingly, insulin secretion per cell on scaffolds coated with Matrigel ($0.52\pm0.15$ $\mu IU/10^3$ cells) and collagen IV ($0.58\pm0.18$ $\mu IU/10^3$ cells) failed to respond to the individual glucose challenges. Using the stimulation index, scaffold cultures pre-coated with ECM proteins did not have a significant improvement in β-cell function compared to naked scaffolds ($0.63\pm0.03$ for PLG with Matrigel, $1.15\pm0.15$ for PLG with laminin, $1.02\pm0.17$ for PLG with collagen IV compared to $1.34\pm0.20$ for PLG, n=3) (FIG. 6D). These findings indicate the initial introduction of ECM prior to cell seeding on the scaffold does not substantially improve maturation at the end of the scaffold culture, which could be potentially due to deposition of cell-secreted matrix proteins throughout the culture.

Example 8

This example provides additional details on the materials and methods used in the above examples.

Protein adsorption to scaffolds: For coating scaffolds with ECM proteins, scaffolds were fabricated and then disinfected in 70% ethanol and dried again before being placed into individual wells of a 24-well tissue culture dish. Proteins were then coated per manufacturer's recommendations to be consistent with our previous report that demonstrated enhancement in islet function following transplantation on ECM protein-modified scaffolds [Salvay et al., Transplantation. 85 (2008) 1456-1464. doi:10.1097/TP.0b013e31816fc0ea; and Yap et al., Tissue Eng. Part A. 19 (2013) 2361-2372. doi:10.1089/ten.tea.2013.0033]. Collagen IV (25 μL at 1 mg/mL; Sigma), laminin-332 (25 μL at 1 mg/mL, formerly termed laminin-5 and hereafter referred to as "laminin"; Sigma), 25 μL of Matrigel (Corning, Cat #: 354277) or PBS were added to the scaffold. The scaffolds were then incubated at 37° C. for 1 h, followed by the addition of 25 μL of the same component to each scaffold. Scaffolds were then incubated with 95% humidity at 37° C. overnight to facilitate protein adsorption to the scaffold surface. Prior to cell seeding, control and ECM-coated scaffolds were washed in cell culture media.

Cell viability: The viability of cells on the scaffolds was qualitatively assessed using a Live/Dead® viability/cytotoxicity kit (Life Technologies). Cells were stained with a solution consisting of 5 μl of 4 mM acetomethoxy derivate of calcein (calcein-AM) and 20 μL of 2 mM ethidium homodimer-1 (EthD-1) in 10 ml of sterile PBS. Cells cultured on microporous scaffolds were incubated at 37° C. and 5% $CO_2$ in the live/dead solution for 30 min, followed by a wash in PBS and then the viability was assessed using a fluorescent microscope (Olympus, Center Valley, PA, United States).

qRT-PCR Analysis: For gene expression analysis, cell-laden scaffolds were mechanically homogenized in Trizol® reagent (Life Technologies), and RNA was isolated using Direct-Zol™ RNA MiniPrep Plus (Zymo Research Corporation, Orange, CA, USA) according to the manufacturer's instructions. RNA concentration was determined using a NanoDrop spectrophotometer. The iScript™ Reverse Transcription Supermix was used to transcribe RNA into cDNA. Universal RT microRNA PCR assays were performed using SYBR Green MasterMix Universal RT (Exiqon), according to the manufacturer's instructions. The amplification profile was assessed using a LightCycler® 480 (Roche, Germany). Gene expression was quantified using the ΔΔCt method and fold change was calculated using the formula $2^{-\Delta\Delta Ct}$. Values for the genes of interest were normalized to the housekeeping gene (GAPDH) followed by normalization to marker expression in pluripotent hPSCs. Primers of Pancreatic Differentiation Markers used for qPCR analysis are listed in Table 1.

| gene | primer | sequence (5' to 3') | SEQ ID NO: |
|------|--------|---------------------|------------|
| PDX1 | forward | CCTTTCCCATGGATGAAGTC | 1 |
| PDX1 | reverse | CGTCCGCTTGTTCTCCTC | 2 |
| Nkx6.1 | forward | GGGGATGACAGAGAGTCAGG | 3 |
| Nkx6.1 | reverse | CGAGTCCTGCTTCTTCTTGG | 4 |
| MafA | forward | GAGAGCGAGAAGTGCCAACT | 5 |
| MafA | reverse | TTCTCCTTGTACAGGTCCCG | 6 |
| Insulin | forward | TTCTACACACCCAAGACCCG | 7 |
| Insulin | reverse | CAATGCCACGCTTCTGC | 8 |
| Glucagon | forward | TGCTCTCTCTTCACCTGCTCT | 9 |
| Glucagon | reverse | AGCTGCCTTGTACCAGCATT | 10 |
| ECAD | forward | TTGACGCCGAGAGCTACAC | 11 |
| ECAD | reverse | GACCGGTGCAATCTTCAAA | 12 |
| PCSK1 | forward | CTCTGGCTGCTGGCATCT | 13 |
| PCSK1 | reverse | CGGGTCATACTCAGAGGTCC | 14 |

-continued

| gene | primer | sequence (5' to 3') | SEQ ID NO: |
|------|--------|---------------------|------------|
| G6PC2 | forward | TGGTATGTCATGGTAACCGC | 15 |
| G6PC2 | reverse | CACTCCAAAGAAATGACCAGG | 16 |

Immunostaining: Immunostaining of in vitro cell differentiation was performed on end-stage β-cell clusters. Scaffold cultures were cryopreserved in isopentane and cooled on dry ice, while suspension clusters were fixed with 4% paraformaldehyde (Electron Microscopy Sciences; Hatfield, PA, United States) then embedded within OCT embedding medium (Tissue-Tek, Sakura Finetech, Torrance, CA) and cryosectioned to 14 μm sections. Scaffold tissue sections and cells differentiated in suspension cultures were fixed with 4% paraformaldehyde for 30 min, blocked and permeabilized for 30-min with staining buffer (5% donkey serum, Jackson Immunoresearch; 017-000-121) and 0.1% Triton-X 100 (Acros Organics; 327371000 in PBS), stained overnight with primary antibodies at 4° C., stained for 4 hr with secondary antibodies at 4° C., and treated with mounting solution DAPI Fluoromount-G (SouthernBiotech; 0100-20). Digital images were acquired with a MicroFire digital camera (Optronics, Goleta, CA) connected to an Olympus BX-41 fluorescence microscope (Olympus, Center Valley, PA, United States). Image quantification was conducted with MATLAB software using an object-based colocalization analysis. DAPI$^+$ cells were identified per total area of the sectioned tissue and quantified by applying Otsu's thresholding method, the watershed transform, and individual cluster thresholding. Then, each cell's colocalization with immunofluorescent markers was quantified. For confocal imaging, whole tissue samples were fixed in 4% paraformaldehyde then stained with primary and secondary antibodies as described above. The labeled samples were then cleared in Murray's clear solution for optical clearing for 45 min before being imaged via confocal microscopy (Nikon A1Si laser scanning confocal microscope, Nikon Instruments Inc, Tokyo, Japan).

Primary antibody solutions were made in staining buffer with the following antibodies at a 1:250 dilution: guinea pig-anti-Insulin (Dako, A05654), mouse-anti-ECAD (Novus Biologicals; 7H12), rabbit-anti-Collagen IV (Thermo Fisher, PA128534), rabbit-anti-Laminin (Thermo Fisher, PA516287), rabbit-anti-Fibronectin (Abcam, AB23750). Secondary antibody solutions were made in staining buffer with the following antibodies at 1:500 dilution:anti-guinea pig-alexa fluor 488 (Life Technologies; A11073), anti-mouse-alexa fluor 555 (Life Technologies, A31570), anti-rabbit-alexa fluor 555 (Life Technologies, A31572).

Static Glucose-Stimulated Insulin Secretion Assay: For GSIS testing, scaffold cultures and suspension clusters were first washed twice with KRB buffer (125 mM NaCl, 3 mM KCl, 1.2 mM CaCl$_2$ 1.2 mM MgSO$_4$, 1 mM NaH$_2$PO$_4$, 22 mM NaHCO$_3$, 10 mM HEPES (Gibco; 15630-080), and 0.1% BSA), exposed to a basal level of glucose (2.8 mM) in a 24 well plate for 30 minutes, then transferred to a second, fresh basal glucose solution and incubated for an hour. Samples from this basal glucose solution were retained. The cells were then washed in fresh basal level glucose for 10 minutes and next exposed to a high-level glucose concentration (28 mM) for an hour. Samples from the retained second basal glucose solution and high-level glucose solution were collected to measure insulin levels using a Human Insulin ELISA kit (Mercodia Inc. 10-1113-01). The cells were single cell dispersed by TrypLE treatment, counted in a hemacytometer, and viable cell counts were used to normalize insulin secretion.

Statistics: All statistical analyses were conducted using Prism graphing and data analysis software (GraphPad Software, Inc., La Jolla, CA, United States). Values were reported as the mean±SEM. n indicates the total number of biological replicates.

Example 9

This example provides a discussion of the experimental results described herein.

The influence of ECM-coated scaffolds on β-cell maturation was evaluated as well the role of the matrix in cellular assembly and differentiation. Finally, the maturation and function of these cells was assessed through glucose stimulated insulin secretion assays. These studies provide insight on cell-cell and cell-matrix interactions that influence the differentiation of hPSCs to β-cells on microporous scaffolds, which suggest this platform for biomanufacturing the cells as a therapy for T1D.

Our findings demonstrate that microporous scaffolds formed from synthetic materials can serve as a supportive matrix to promote the differentiation of hPSC-derived pancreatic progenitors toward insulin-producing glucose-responsive β-cells in vitro. Synthetic materials were used for these studies as they provide flexibility in synthesis and modification, have been widely applied for islet transplantation [Salvay et al., 2008, supra, Yap et al., 2013, supra, and Blomeier et al., Transplantation. 82 (2006) 452-459. doi: 10.1097/01.tp.0000231708.19937.21] and are generally easy to manufacture for large scale production. The scaffolds were designed to have a high porosity, a fully interconnected geometry, structural integrity, and a defined three-dimensional shape. Additionally, the microporous structure allows the 3D organization of cells into β-cell clusters, provides a high surface area-to-volume ratio for polymer-cell interactions, and allows nutrients to diffuse into the scaffold to support the growth of the seeded cells.

hPSC-derived β-cells cultured on the scaffold showed significantly increased gene expression levels of pancreatic endocrine hormones, insulin and glucagon, relative to pancreatic progenitors. Furthermore, the gene expression of β-cell maturation markers (MAFA, PCSK1, and G6PC2) were increased on the scaffold compared to the suspension clusters. β-cell maturation was further investigated through glucose-responsive functional tests that demonstrated cells cultured on the scaffold had higher insulin secretion than suspension clusters. Immunohistochemical stains show that the percentage of Ins$^+$ cells in the PLG scaffold culture was increased compared to suspension cultures, suggesting that the scaffold cultures may have a higher efficiency at generating β-cells during differentiation.

Despite their similar biomaterial design, the microporous PLG and PEG scaffolds also exhibited a few differences in how they influenced cell differentiation. Relative to suspension clusters, PEG scaffold cultures showed a more significant increase in the gene expression of β-cell maturation markers than PLG scaffolds. On the other hand, when investigating cell-cell interactions, only ECAD gene expression from PLG scaffold cultures showed a significant increase relative to the suspension cultures. This difference could have played a role in the higher insulin secretion observed in PLG scaffolds versus PEG scaffold cultures.

Additionally, PLG scaffolds are a degradable material, unlike PEG, which could play a role in improved function as these scaffolds may allow for remodeling of the local environment. Both PEG and PLG are amenable to our fundamental objective-supporting β-cell maturation in a 3D environment-yet PLG and PEG have some differences. These variances may be due to their different mechanical and physical properties (i.e. hydrophobicity and protein adhesion) that could influence cell-cell and cell-matrix interactions.

In this study, we also show microporous scaffolds provide an environment conducive to controlling the size of the structures that could be essential for maturation. The size of transplanted islets has been previously reported to impact insulin secretion and viability [Lehmann et al., Diabetes. 56 (2007) 594-603. doi:10.2337/db06-0779, Farhat et al., Islets. 5 (2013) 87-94. doi:10.4161/isl.24780; and Mendelsohn et al., Acta Biomater. 8 (2012) 4278-4284. doi:10.1016/j.act-bio.2012.08.010]. Small islet clusters can exhibit low amounts of insulin secretion, which has been attributed to limited cell-cell contact, while excessively large clusters are considered to have limitations from nutrient availability [Mendelsohn et al., Acta Biomater. 8 (2012) 4278-4284. doi:10.1016/j.actbio.2012.08.010]. Based on these results with islets, the influence of pore size, which would determine the hPSC-derived β-cell cluster size, was investigated. Our results suggest that clusters forming in pores with diameters greater than 250 μm maximized maturation toward β-cells. These results may reflect a contribution from the surface area to maturation. In addition, a scaffold with larger pores could have a greater interconnected porosity, thus, aiding diffusion of growth media as well as enabling a more uniform distribution of seeded cells into the scaffold. The seeding density, in combination with the pore size, was also shown to be critical for promoting cell-cell interactions. At low seeding densities, the cells were observed to primarily attach to the walls of the pores. However, increasing the cell density increasingly favored cluster formation and cell-cell interactions within the pore. Expression of E-cadherin was increased within scaffold culture relative to suspension culture, and E-cadherin staining was observed primarily between cells within the pores and not at the material surface. E-cadherin is a key player in maturation as studies have shown that E-cadherin immune-neutralization reduces both basal and glucose-stimulated insulin secretion [Rogers et al., Cell. Physiol. Biochem. 20 (2007) 987-994. doi: 10.1159/000110459]. Collectively, the microporous scaffold can be employed to control the formation of clusters, and to favor cell-cell interactions that are influential in maturation.

Protocols generally rely on hPSCs to spontaneously cluster in suspension resulting in the clusters varying in size [Jiang et al., STEM CELLS. 25 (2007) 1940-1953. doi: 10.1634/stemcells.2006-0761; Shim et al., Diabetologia. 50 (2007) 1228-1238. doi:10.1007/s00125-007-0634-z; and Phillips et al., Stem Cells Dev. 16 (2007) 561-578. doi: 10.1089/scd.2007.0029], though efforts have started to focus on establishing a mechanism for controlling the size of the end-stage β-cell clusters due to the influence on long-term viability and the secretion of sufficient insulin [Velazco-Cruz et al., Stem Cell Rep. (2019). doi:10.1016/j.stemcr.2018.12.012; and Nair et al., Nat. Cell Biol. 21 (2019) 263. doi:10.1038/s41556-018-0271-4]. While physical manipulation and shear have largely been employed to provide control of cluster size, the pores of the scaffold can provide direct control on cluster size, which may be advantageous for manufacturing. For large scale cell manufacturing in industrial or clinical settings, shear stress has been associated with challenges due to low cell viability and differentiation potential or abnormal morphology or gene expression [Serra et al., Trends Biotechnol. 30 (2012) 350-359; Sargent et al., Biotechnol. Bioeng. 105 (2010) 611-626. doi:10.1002/bit.22578; and Zhao et al., J. Cell. Physiol. 219 (2009) 421-429. doi:10.1002/jcp.21688]. In embodiments of the present disclosure, the scaffold serving as a strategy to control cell cluster size can protect against adverse effects of shear during large scale manufacturing.

Similar to cell-cell interactions, interactions between stem cells and the extracellular matrix can induce lineage-specific differentiation and support the function of differentiated cells by providing a composite set of chemical and structural signals [Riopel et al., Front. Biosci. Landmark Ed. 19 (2014) 77-90]. Herein, we report that differentiating cells deposited ECM proteins within the scaffold, with the composition resembling that found in the basement membrane around islets. Furthermore, we found ECM proteins were homogeneously distributed throughout the scaffold culture, thus, available for interaction with β-cells throughout the cluster. By culturing maturing β-cell clusters in microporous scaffolds versus suspension, cells are able to maintain a 3D morphology while interacting with a supportive matrix. A supportive matrix with which the clusters can interact may enhance cell maturation, as studies have shown ECM proteins such as collagen IV support the formation of cell structures, while also stimulating cell surface receptors to influence pancreatic cell processes [Riopel et al., 2014, supra]. Scaffold cultures also offer the opportunity to modify the local microenvironment surrounding the β-cell cluster that can be used to investigate the role of cell-matrix interactions during differentiation. Finally, suspension clusters undergo manipulation during the transplantation process that may disrupt cell-cell and cell-matrix interactions. Whereas, for cells cultured in scaffolds, the scaffolds maintain their niche that has been established within the pores, which can support the cell structures during transplantation.

Matrix deposition by the cells is likely a key step in maturation, as key integrins change over developmental stages [Darribère et al., Biol. Cell. 92 (2000) 5-25]. This deposition of matrix initiates the formation of a niche, which is normally present in islets and influences maturation and function. Attachment of cells to ECM may also benefit β-cells by maintaining tissue architecture and preserving specific intercellular relationships within the pores. Interestingly, scaffolds coated with either collagen IV, laminin or Matrigel showed comparable gene expression levels of maturation markers to naked scaffolds relying on cell-secreted ECM, which contained collagen IV, laminin and fibronectin. This was supported by the analysis of glucose-responsive insulin secretion on ECM coated scaffolds and naked scaffolds that showed β-cell function was similar across all conditions as well. These results suggest the matrix deposited by the cells on the PLG scaffold has the potential to mimic more of the complex niche environment during pancreatic development compared to the individual ECM proteins, and the ECM deposition may mask the impact of the adsorbed ECM proteins.

This research demonstrates that scaffolds have the potential to serve as a component within the process of manufacturing β-cells. The scaffold design can be tuned to control cluster size, promote cell-cell interactions and permit ECM deposition on the scaffold to create a supportive niche. Similar to organoid development in three-dimensional cultures, the pancreatic progenitors establish a functional niche during in vitro scaffold culture. Furthermore, the scaffolds are formed from materials that have been used in vivo, and thus the cell-material construct can be directly transplanted, which has the added advantage of maintaining the niche that has developed within the scaffold. Collectively, microporous scaffolds demonstrate the feasibility as a biomanufacturing platform to generate insulin-producing glucose-responsive β-cells.

REFERENCES

The following references are cited outside of the Examples according to the numbering below:

[1] Cryer P E. Diabetes. 2008; 57:3169-76.
[2] Pambianco et al., Diabetes. 2006; 55:1463-9.
[3] Shapiro et al., N Engl J Med. 2000; 343:230-8.
[4] Bruin et al., Diabetologia. 2013.
[5] Pagliuca et al., Development. 2013; 140:2472-83.
[6] Pagliuca et al., Cell. 2014; 159:428-39.
[7] Rezania et al., Diabetes. 2012; 61:2016-29.
[8] Rezania et al., Stem Cells. 2013.
[9] Rezania et al., Nature Biotechnology. 2014; 32:1121-33.
[10] Vegas et al., Nature Medicine. 2016; 22:306-11.
[11] Weizman et al., Biomaterials Science. 2014; 2:1706-14.
[12] Kroon et al., Nat Biotechnol. 2008; 26:443-52.
[13] Zhang et al., Cell Res. 2009; 19:429-38.
[14] Blomeier et al. Transplantation. 2006; 82:452-59.
[15] Salvay et al., Transplantation. 2008; 85:1456-64.
[16] Yap et al., Tissue Eng Part A. 2013.
[17] Hlavaty et al., American Journal of Transplantation. 2014; 14:1523-32.
[18] Gibly et al., Biomaterials. 2011; 32:9677-84.
[19] Gibly et al., Cell Transplantation. 2013; 22:811-9.
[20] Dye, et al., *eLife* 5 (Sep. 28, 2016): e19732. doi: 10.7554/eLife.1973
[21] Zhu et al., Diabetes. 2016; 65:699-709.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

Preferred embodiments of this disclosure are described herein, including the best mode known to the inventors for carrying out the disclosure. Variations of those preferred embodiments may become apparent to those of ordinary skill in the art upon reading the foregoing description. The inventors expect skilled artisans to employ such variations as appropriate, and the inventors intend for the disclosure to be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

---

What is claimed is:

1. An in vitro method of preparing insulin-producing cell clusters, comprising:

a) seeding pancreatic progenitor cells onto a three-dimensional, porous scaffold comprising a synthetic polymer at a seeding density greater than 12.5 million cells per $cm^3$ of scaffold and less than 250 million cells per $cm^3$ scaffold, wherein the scaffold comprises a plurality of pores having an average pore diameter of 250 μm to 425 μm; and b) culturing and differentiating the cells on the scaffold in vitro for at least 4 days to obtain insulin-producing cell clusters, wherein at least a portion of each insulin-producing cell cluster is in a pore of the scaffold.

2. The method of claim 1, wherein the seeding density is greater than 25 million cells per $cm^3$ scaffold and less than 125 million cells per $cm^3$ of scaffold.

3. The method of claim 1, wherein step (a) comprises seeding a volume of a solution comprising the pancreatic progenitor cells onto the three-dimensional, porous scaffold, wherein the volume is not more than 30 μL.

4. The method of claim 1, wherein the pancreatic progenitor cells are Stage 4 pancreatic progenitor cells expressing PDX1 and NKX6.1, optionally, wherein the Stage 4 pancreatic progenitor cells expressing PDX1 and NKX6.1 are derived from pluripotent stem cells.

5. The method of claim 4, wherein the pluripotent stem cells are human pluripotent stem cells (hPSCs).

6. The method of claim 1, wherein, prior to step (a), the method comprises treating the pancreatic progenitor cells with a cell dissociation agent.

7. The method of claim 1, wherein step (b) comprises culturing the cells on the scaffold in vitro for 4 days to 24 days to obtain insulin-producing cell clusters.

8. The method of claim 1, wherein the cells seeded onto the scaffold express and secrete extracellular matrix (ECM) proteins within the scaffold, wherein the ECM proteins comprise one or more of collagen IV, laminin and fibronectin.

9. The method of claim 1, wherein the scaffold does not contain and is not coated with collagen, laminin, or fibronectin prior to the seeding step (a).

10. The method claim 1, wherein the scaffold is fabricated with salt porogens having an average diameter of 250 μm to 425 μm.

11. The method of claim 1, wherein the scaffold comprises polyethylene glycol.

12. The method of claim 1, wherein the synthetic polymer comprises poly(lactide-co-glycolide) (PLG) and the average pore diameter is about 370 μm±37 μm.

13. The method of claim 1, wherein the synthetic polymer comprises poly(ethylene glycol) (PEG), poly(lactide-co-glycolide) (PLG), or a combination thereof.

14. A method of treating a patient with an insulin deficiency, the method comprising:

a. seeding pancreatic progenitor cells onto a three-dimensional, porous scaffold comprising a synthetic polymer at a seeding density greater than 12.5 million cells per $cm^3$ of scaffold and less than 250 million cells per $cm^3$ of scaffold, wherein the scaffold comprises a plurality of pores having an average pore diameter of 250 μm to 425 μm;

b. culturing and differentiating the pancreatic progenitor cells on the scaffold in vitro for at least 4 days into insulin-producing cell clusters, wherein at least a portion of each insulin-producing cell cluster is in a pore of the scaffold; and c. administering the scaffold comprising the insulin-producing cell clusters to the patient with the insulin deficiency.

*    *    *    *    *